United States Patent [19]
Van Aken et al.

[11] Patent Number: 5,591,830
[45] Date of Patent: Jan. 7, 1997

[54] DETECTION OF COMPLEXES WHICH INCLUDE BASEMENT MEMBRANE COMPONENTS AS DIAGNOSTIC OF CANCER AND OTHER DISEASES

[75] Inventors: Morgan Van Aken; Stefan L. Paskell, both of Bainbridge Island, Wash.

[73] Assignee: Bainbridge Sciences, Inc., Redmond, Wash.

[21] Appl. No.: 456,855

[22] Filed: Jun. 1, 1995

Related U.S. Application Data

[63] Continuation of Ser. No. 178,219, Jan. 6, 1994, Pat. No. 5,512,657, which is a continuation of Ser. No. 96,490, Jul. 23, 1993, abandoned, which is a continuation-in-part of Ser. No. 721,756, Jun. 26, 1991, Pat. No. 5,264,370, which is a continuation-in-part of Ser. No. 283,397, Dec. 12, 1988, abandoned.

[51] Int. Cl.$^6$ .............................. C07K 16/00; C07K 16/18
[52] U.S. Cl. ................................. 530/388.85; 530/387.1; 530/388.1; 530/388.2; 435/7.23
[58] Field of Search ........................ 530/387.1, 388.1, 530/388.2, 388.85; 435/7.23

[56] References Cited

U.S. PATENT DOCUMENTS

| | | | |
|---|---|---|---|
| 4,264,766 | 4/1981 | Fischer | 524/556 |
| 4,340,581 | 7/1982 | Timpl | 424/1.57 |
| 4,376,110 | 3/1983 | David et al. | 435/5 |
| 4,452,901 | 6/1984 | Gordon et al. | 435/7.92 |
| 4,497,900 | 2/1985 | Abram et al. | 435/7.36 |
| 4,565,789 | 1/1986 | Liotta et al. | 436/504 |
| 4,609,629 | 9/1986 | Timpl | 436/512 |
| 4,628,027 | 12/1986 | Gay | 435/7.23 |
| 4,689,220 | 8/1987 | Sturmer et al. | 530/389.2 |
| 4,829,000 | 5/1989 | Kleinman et al. | 435/240.23 |
| 4,847,199 | 7/1989 | Snyder et al. | 435/7.34 |
| 5,147,782 | 9/1992 | Brocks et al. | 435/7.21 |
| 5,354,666 | 10/1994 | Danielson et al. | 435/70.3 |

FOREIGN PATENT DOCUMENTS

3743402A1   7/1988   Germany.

OTHER PUBLICATIONS

Albrechtsen et al., "Basement Membrane Changes in Breast Cancer Detected by Immunohistochemical Staining for Laminin," *Cancer Res.* 41:5076–5081, 1981.

Alitalo et al., "Extracellular Matrix Proteins Characterize Human Tumor Cell Lines," *Int. J. Cancer* 27:755–761, 1981.

Askenasi, "Urinary hydroxylysine and hydroxylysyl glycoside excretions in normal and pathologic states," *J. Lab. Clin. Med.* 83(4):673–679, 1974.

Babaian et al., "Immune Complexes in Urine and Serum of Patients With Bladder Cancer," *J. Urol.* 131:463–466, 1984.

Barsky et al., "Loss of Basement Membrane Components by Invasive Tumors but Not by Their Benign Counterparts," *Lab. Invest.* 49:140–147, 1983.

Bisbee and Kelleher, "A Method for Measuring Hydroxylsine and Glycosylated Hydroxylsines in Urine and Protein Hydrolysates", *Clin. Chim. Acta* 90:29–36, 1978.

Bowen-Pope et al., "Production of platelet–derived growth factor–like molecules and reduced expression of platelet–derived growth factor receptors accompany transformation by wide spectrum of agents," *Proc. Natl. Acad. Sci. USA* 81:2396–2400, 1984.

Bowman et al., "Novel Urinary Fragments from Human Basement Membrane Collagen," *J. Biol. Chem.* 255(19):9484–9489, 1980.

Brocks et al., "Type IV collagen antigens in serum of diabetic rats: a marker for basement membrane collagen biosynthesis," *Diabetologia* 28:928–932, 1985.

Brocks et al. "Radioimmunoassay of Laminin in Serum and Its Application to Cancer," *Clin. Chem.* 32(5):787–791, 1986.

Brooks et al., "Human lymphocyte markers defined by antibodies derived from somatic cell hybrids," *Clin. Exp. Immunol.* 39:477–485, 1980.

Brown et al., "Protein Antigens of Normal and Malignant Human Cells Identified by Immunoprecipitation with Monoclonal Antibodies," *J. Biol. Chem.* 255(11):4980–4983, 1980.

Burtin et al., "Antigens of the Basement Membrane and the Peritumoral Stroma in Human Colonic Adenocarcinomas: An Immunofluorescence Study," *Int. J. Cancer* 30:13–20, 1982.

Cederholm et al., "Patients with IgA nephropathy have circulating anti–basement membrane antibodies reacting with structures common to collagen I, II, and IV," *Proc. Natl. Acad. Sci. USA* 836151–6155, 1986.

Conn et al., "Basement Membranes in Urothelial Carcinoma," *Br. J. Urology* 60:536–542, 1987.

Csákó et al., "Similarities and dissimilarities between the binding ability of Clq and collagen," *Clin. exp. Immunol.* 44:181–190, 1981.

Csako et al., "On the Reactivity of Corneal Collagen and Subcomponent Clq of the Complement System with Human Platelets and IgG–Coated Latex Particles," *Exp. Eye Res.* 36:403–414, 1983.

Dixit, "Isolation, Purification and Characterization of Intact and Pepsin–Derived Fragments of Laminin From Human Placenta," *Connective Tissue Research* 14:31–40, 1985.

(List continued on next page.)

*Primary Examiner*—Toni R. Scheiner
*Attorney, Agent, or Firm*—Seed and Berry LLP

[57] ABSTRACT

Isolated complexes (which include basement membrane components), antibodies to such complexes or polypeptide constituents thereof, and methods for detecting such complexes or constituents are disclosed. Detection of such complexes in a biological sample by immunological and non-immunological methods allows the diagnosis of a variety of diseases, including cancers, collagen degenerative diseases, and hepatitis. Suitable biological samples include urine, cervical secretions, bronchial aspirates, sputum, saliva, feces, serum, synovial fluid, and cerebrospinal fluid.

11 Claims, 25 Drawing Sheets

OTHER PUBLICATIONS

Dresden et al., "Collagenolytic Enzymes in Human Neoplasms," *Cancer Research* 32:993–996, 1972.

Eeckhout et al., "Agglutination of IgG–Coated Particles By Collagen," *FEBS Lett.* 107:69–72, 1979.

Fessler et al., "Characterization of the Procollagen IV Cleavage Products Produced by a Specific Tumor Colloagenase," *J. Biol. Chem.* 259:9783–9789, 1984.

Galfré et al., "Rat x rat hybrid myelomas and a monoclonal anti–Fd portion of mouse IgG," *Nature* 277:131–133, 1979.

Garbisa et al., "Quantitation of Basement Membrane Collagen Degradation By Living Tumor Cells in Vitro," *Cancer Letters* 9:359–366, 1980.

Huang et al., "Collagenase Activity in Cultures of Rat Prostrate Carcinoma," *Biochim. Biophys. Acta* 570:149–156, 1979.

Knudsen, "Proteins Transferred to Nitrocellulose for Use as Immunogens," *Anal. Biochem.* 147:285–288, 1985.

Kobayashi et al., "Circulating Immune Complexes in Patients with Bladder Cancer and Other Malignancies of the Urogenital Tract," *Urol. Int.* 39:232–235, 1984.

Köhler and Milstein, "Derivation of specific antibody–producing tissue culture and tumor lines by cell fusion," *Eur. J. Immunol.* 6:511–519, 1976.

Köhler and Milstein, "Continuous cultures of fused cells secreting antibody of predefined specificity," *Nature* 256:495–497, 1975.

Krane et al. "Urinary Excretion of Hydroxylysine and its Glycosides as an Index of Collagen Degradation," *J. Clin. Invest.* 59:819–827, 1977.

Linsenmayer et al., "Basement membrane structure assembly: inferences from immunological studies with monoclonal antibodies," *Chem. Abst.* 101:148327m, 1984.

Liotta et al., "Biochemical Interactions of Tumor Cells With the Basement Membrane," *Ann. Rev. Biochem.* 55:1037–1057, 1986.

Liotta et al., "Partial Purification and Characterization of a Neutral Protease Which Cleaves Type IV Collagen," *Biochemistry* 20:100–104, 1981.

Liotta et al., "Degradation of Basement Membrane by Murine Tumor Cells," *J. Natl. Cancer Inst.* 58:1427–1431, 1977.

Liotta et al., "Metastatic potential correlates with enzymatic degradation of basement membrane collagen," *Nature* 284:67–68, 1980.

McCabe et al., "A Diagnostic–Prognostic Test for Bladder Cancer Using a Monoclonal Antibody–based Enzyme–linked Immunoassay for Detection of Urinary Fibrin(ogen) Degradation Products," *Cancer Res.* 44:5886–5893, 1984.

McCarthy et al., "Localization and Chemical Synthesis of Fibronectin Peptides with Melanoma Adhesion and Heparin Binding Activities," *Biochemistry* 27:1380–1388, 1988.

Mellon et al., "Increased Concentrations of Basement Membrane Collagen Fragment in Urine of Diabetic Mice," *Biochem. Genet.* 22:631–639, 1985.

Nagai et al., "Characterization of fibronectin metabolites in normal rat urine," *Biochim. Biophys. Acta* 967:176–182, 1988.

Nakajima et al., "Basement membrane degradative enzymes as possible markers of tumor metastasis," in *Cancer Metastasis: Experimental and Clinical Strategies,* Alan R. Liss, Inc. 1986, pp. 113–122.

Oellerich, "Enzyme–Immunoassay: A Review," *J. Clin. Chem. Clin. Biochem.* 22:895–904, 1984.

Palm et al., "Alternative Model for the Internal Structure of Laminin," *Biochemistry* 24:7753–7760, 1985.

Pernice and Sedlacek, "Antigen–Specific Detection of Soluble Immune Complexes By a Solid Phase Specific Antibody System," *J. Immunol. Methods* 28:33–40, 1979.

Prockhop and Kivirikko, "Hydroxyproline and the Metabolism of Collagen," in B. S. Gould, ed., *Treatise on Collagen,* vol. 2A, Academic Press, pp. 215,246.

Raines and Ross, "Platelet–derived Growth Factor," *J. Biol. Chem.* 257:5154–5160, 1982.

Rao et al., "Characterization of the 200 KD Subunit and Protease Resistant Fragment of Laminin By Using Monoclonal Antibodies and Peptide Mapping Studies," *Fed. Proc.* p. 418, Abstr. No. 44.

Rao et al., "Binding Domain for Laminin on Type IV Collagen," *Biochem. Biophys. Res. Comm.* 128:45–52, 1985.

Robertson and Williams, "In vitro Evidence of Neutral Collagenase Activity in an Invasive Mammalian Tumour," *Nature* 221:259–260, 1969.

Rohde et al., "Immunochemical Characterization of the Basement Membrane Glycoprotein Laminin," *Eur. J. Biochem.* 102:195–201, 1979.

Rucklidge et al., "Evidence for Renal Tubular Resorption of Collagen Fragments from Immunostaining of Rat Kidney with Antibodies Specific for Denatured Type I Collagen," *Collagen Res.* 6:185–193, 1986.

Sakai et al., "Production and characterization of a monoclonal antibody to human Type IV collagen," *Chem. Abst.* 97:179907d, 1982.

Salo et al., "Secretion of Basement Membrane Collagen Degrading Enzyme and Plasminogen Activator by Transformed Cells—Role in Metastasis," *Int. J. Cancer* 30:669–673, 1982.

Sas et al., "Clearing and release of basement membrane proteins from substrates by metastatic tumor cell variants," *Chem. Abst.* 105:22432f, 1986.

Savolainen et al., "Serum concentrations of the N–terminal propeptide of type III procollagen and two type IV collagen fragments and gene expression of the respective collagen types in liver in rats with dimethylnitrosamine–induced hepatic fibrosis," *Biochem. J.* 249:753–757, 1988.

Scheinman and Tsai, "Monoclonal antibody to type IV collagen with selective basement membrane localization," *Chem. Abst.* 100:99259j, 1984.

Schneider et al., "Studies of Human Urinary Protein Fragments from Extracellular Matrix Proteins," *Renal Physiol.* 6:157–162, 1983.

*The Sigma Chemical Co.,* St. Louis, Mo., p. 1027, 1986.

Skubitz et al., "Localization of a Tumor Cell Adhesion Domain of Laminin by a Monoclonal Antibody," *Exp. Cell Res.* 173:349–369, 1987.

Skubitz and Furcht, "Characterization of Monoclonal Antibodies Against Laminin Fragments," *J. Cell Biol.* 103:94, 1986.

Stanker et al., "One–Step Purification of Mouse Monoclonal Antibodies from Ascites Fluid by Hydroxylapatite Chromatography," *J. Immunol. Methods* 76:157–169, 1985.

Starkey et al., "Interaction of Metastasis Tumor Cells with Bovine Lens Capsule Basement Membrane," *Cancer Res.* 44:1585–1594, 1984.

Steinberg et al., "Establishment and Transformation Diminish the Ability of Fibroblasts to Contact a Native Collagen Gel," *J. Cell Biol.* 87:304–308, 1980.

Sundarraj and Willson, "Monoclonal antibody to human basement membrane collagen type IV," *Chem. Abst.* 97:196637h, 1982.

Takahashi et al., "A Monoclonal Antibody to Human Transitional Cell Carcinoma of the Bladder: Production and Characterization," *J. Urol.* 138:207–211, 1987.

Taubman et al., "Radioimmunoassay of Procollagen in Serum of Patients with Paget's Disease of Bone (39380)," *Proc. Soc. Exp. Biol. Med.* 152:284–287, 1976.

Thorgeirsson et al., "Cancer Cells, Components of Basement Membranes, and Proteolytic Enzymes", *Int. Rev. Exp. Pathol.* 27:203–234, 1985.

Timpl and Rohde, "Laminin—A Glycoprotein from Basement Membranes," *J. Biol. Chem.* 254:9933–9937, 1979.

Towbin et al., "Electrophoretic transfer of proteins from polyacrylamide gels to nitrocellulose sheets: Procedure and some applications," *Proc. Natl. Acad. Sci. USA* 76:4350–4354, 1979.

Vartio et al., "Monoclonal Antibodies in Analysis of Cathepsin G–Digested Proteolytic Fragments of Human Plasma Fibronectin," *J. Immunol. Methods* 55:309–318, 1982.

Wajsman et al., "Further Study of Fibrinogen Degradation Products in Bladder Cancer Detection," *Urology* 12:659–661, 1978.

Weiss and Klein, "The Quantitative Relationship of Urinary Peptide Hydroxyproline Excretion to Collagen Degradation," *J. Clin. Invest.* 48:1–10, 1969.

Yee and Shiu, "Degradation of Endothelial Basement Membrane by Human Breast Cancer Cell Lines," *Cancer Res.* 46:1835–1839, 1986.

Zimmermann and Vienken, "Electric Field–Induced Cell–to–Cell Fusion," *J. Membrane Biol.* 67:165–182, 1982.

Zucker et al., "Role of different cell proteinases in cancer invasion and cytolysis," *Br. J. Cancer* 52:223–232, 1985.

DETECTION OF COMPLEXES WHICH INCLUDE BASEMENT MEMBRANE COMPONENTS AS DIAGNOSTIC OF CANCER AND OTHER DISEASES

CROSS-REFERENCE TO RELATED APPLICATIONS

This application is a continuation of U.S. patent application to Ser. No. No. 08/178,219, filed Jan. 6, 1994, now U.S. Pat. No. 5,512,657; which is a continuation of Ser. No. 08/096,490, filed Jul. 23, 1993, abandoned; which is a continuation-in-part application to Ser. No. 07/721,756, filed Jun. 26, 1991, issued Nov. 23, 1993 as U.S. Pat. No. 5,264,370; which is a continuation-in-part to Ser. No. 07/283,397, filed Dec. 12, 1988, abandoned.

TECHNICAL FIELD

The present invention relates generally to the diagnosis of diseases, such as cancer, that result in the release of complexes which include basement membrane components. This invention is more particularly related to detection of such complexes or polypeptide components thereof by a variety of methods, including immunological and non-immunological means.

BACKGROUND OF THE INVENTION

A challenge to medicine since its inception has been the development of methods that permit rapid and accurate detection of diseases. Despite advances in diagnostic technology over the years, the current techniques for the diagnosis of many diseases are either inadequate or cost prohibitive for wide scale application. One such illustrative disease is bladder cancer.

As a worldwide problem, it is estimated that there are 50,900 new cases of bladder cancer per year in Western Europe, 3,700 in Japan and 34,000 in North America (WHO 1984), with at least 3 to 4 times this number of patients attending hospitals for follow-up or treatment.

Bladder cancer occurs in two major forms: superficial and invasive. About 70% of superficial tumors will develop one or several recurrences during a five year follow-up period. The major risk is that the tumor will become invasive. Over 90% of bladder cancers are of the transitional cell type.

The invasive form of bladder cancer accounts for approximately 20%–30% of all bladder cancer. Invasive bladder cancer starts in the mucosa lining the bladder, invades through the basement membrane to reach muscle wall, and finally the pelvic tissues and surrounding organs, including local lymph nodes. The outlook depends on the stage, with five-year survivals from 11%–60%. The treatment is by radiotherapy, chemotherapy and surgery.

Patients with invasive bladder tumors are monitored by cytology and check cystoscopy. Although cytology is a non-invasive and less difficult procedure, it can be prone to error or uncertainty. For example, a positive result by cytology may be helpful, but a negative result cannot be taken as evidence of the absence of a tumor. Further, the reporting varies greatly with the cytologists' experience. Cystoscopy is an invasive, expensive and occasionally hazardous procedure, as it is frequently carried out under anesthesia. Despite the uncertainties associated with cystoscopic checks, they are nevertheless still considered by many medical practitioners as the diagnostic tool of choice because of the absence of better tests.

It is generally agreed that reliable tests for the presence of invasive bladder cancer would be helpful not only for initial detection, but also for recurrence and thus aid in the management of patients with histologically proven bladder cancer. If such a reliable test became available, it might then be used to screen persons at risk, e.g., men over 60 years of age. Further, a test not dependent upon gross visualization of a tumor should allow detection at an earlier stage.

Various tumor markers have been evaluated for their potential as tools in the diagnosis of bladder cancer. Positive serum tests for tumor markers, such as carcinoembryonic antigen (CEA), are usually restricted to advanced tumors. Furthermore, urinary infection has been shown to cause false positives.

In addition to the use of tumor markers, several alternative approaches to diagnosing bladder cancer have been suggested. For example, several urinary enzymes have been described with increased urinary activity in bladder cancer. However, none have been found to be useful in a screening test. Similarly, although antibodies against urothelium and its tumors were at first thought to be tissue-specific, some were later shown to be on codevelopmental antigens.

Although the inadequacies and problems in the diagnosis of one particular type of cancer are the focus of the preceding discussion, bladder cancer is merely a representative model. The diagnosis of numerous other diseases, including other types of cancer (such as cervical, lung, colorectal, head and neck cancers) as well as non-cancer conditions, have similar problems.

For example, cervical/uterine cancer is the fourth most common form of cancer in women. In 1992 in the U.S. alone, there were approximately 45,000 new cases and 10,000 deaths. The most commonly used procedure for diagnosis is the pap smear which is used to determine the presence of intraepithelial neoplasms and extent of dysplasia on a grading system from I–V, or the presence of invasive cancers. However, the pap test has a high (20%–30%) false negative rate due to poor sampling or reading. In addition, many individuals have Class II pap smears which are atypical and only 20%–25% of this group progress to invasive cancer. Alternatively, colposcopy/cytology can be used. However, this diagnostic approach is uncomfortable to the patient and expensive.

Thus, there is a need in the art for a method of detecting diseases, such as cancers, that is accurate and cost-effective. The present invention fulfills these needs and further provides other related advantages.

SUMMARY OF THE INVENTION

Briefly stated, the present invention provides isolated complexes, antibodies to such complexes or polypeptide constituents thereof, and methods for detecting such complexes or constituents. In one aspect, the present invention provides substantially pure complexes including basement membrane components. In one embodiment, a complex comprises polypeptides with approximate molecular weights of 165,000; 140,000; 125,000; 98,000; 82,000; 74,000; 55,000; 43,000; 35,000; 26,000; and 16,000 as determined by sodium dodecyl sulfate-polyacrylamide gel electrophoresis ("a complex according to claim 1"). In another embodiment, a complex further includes polypeptides of approximate molecular weights of 245,000 and 190,000 as determined by sodium dodecyl sulfate-polyacrylamide gel electrophoresis ("a complex according to claim 2").

In another aspect, methods are provided for determining the grade of a bladder tumor. In one embodiment, the method comprises the steps of: (a) isolating a urine sample from a warm-blooded animal suspected of possessing a bladder tumor; (b) measuring the amount of a complex according to claim 1 in the sample; (c) detecting the polypeptide composition of the complex; and (d) determining the grade of a bladder tumor based on the amount of the complex and the polypeptide composition of the complex.

In another embodiment, the method for determining the grade of a bladder tumor comprises the steps of: (a) isolating a urine sample from a warm-blooded animal suspected of possessing a bladder tumor; (b) measuring the amount of a first polypeptide of a complex according to claim 1 in the sample, the first polypeptide having an approximate molecular weight of 165,000; 140,000; or 125,000 as determined by sodium dodecyl sulfate-polyacrylamide gel electrophoresis; (c) measuring the amount of a second polypeptide of a complex according to claim 1 in the sample, the second polypeptide having an approximate molecular weight of 98,000; 82,000; 74,000; 55,000; 43,000; 35,000; 26,000; or 16,000 as determined by sodium dodecyl sulfate-polyacrylamide gel electrophoresis; and (d) calculating the ratio of the amount of the first polypeptide to the amount of the second polypeptide, and determining therefrom the grade of the bladder tumor.

In another embodiment, the method for determining the grade of a bladder tumor comprises the steps of: (a) isolating a urine sample from a warm-blooded animal suspected of possessing a bladder tumor; (b) measuring the amount of a first polypeptide of a complex according to claim 1 in the sample by immunological means, the first polypeptide having an approximate molecular weight of 165,000; 140,000; or 125,000 as determined by sodium dodecyl sulfate-polyacrylamide gel electrophoresis; (c) measuring the amount of a second polypeptide of a complex according to claim 1 in the sample by immunological means, the second polypeptide having an approximate molecular weight of 98,000; 82,000; 74,000; 55,000; 43,000; 35,000; 26,000; or 16,000 as determined by sodium dodecyl sulfate-polyacrylamide gel electrophoresis; and (d) calculating the ratio of the amount of the first polypeptide to the amount of the second polypeptide, and determining therefrom the grade of the bladder tumor.

In yet another embodiment, the method for determining the grade of a bladder tumor comprises the steps of: (a) isolating a urine sample from a warm-blooded animal suspected of possessing a bladder tumor; (b) incubating a first aliquot of the sample with an antibody that specifically binds to a first polypeptide of a complex according to claim 1 under conditions and for a time sufficient to allow immunocomplexes to form between the first polypeptide and the antibody, the first polypeptide having an approximate molecular weight of 165,000; 140,000; or 125,000 as determined by sodium dodecyl sulfate-polyacrylamide gel electrophoresis; (c) measuring the amount of the immunocomplexes from step (b), thereby determining the amount of the first polypeptide; (d) incubating a second aliquot of the sample with an antibody that specifically binds to a second polypeptide of a complex according to claim 1 under conditions and for a time sufficient to allow immunocomplexes to form between the second polypeptide and the antibody, the second polypeptide having an approximate molecular weight of 98,000; 82,000; 74,000; 55,000; 43,000; 35,000; 26,000; or 16,000 as determined by sodium dodecyl sulfate-polyacrylamide gel electrophoresis; (e) measuring the amount of the immunocomplexes from step (d), thereby determining the amount of the second polypeptide; and (f) calculating the ratio of the amount of the first polypeptide to the amount of the second polypeptide, and determining therefrom the grade of the bladder tumor.

Another aspect of the present invention provides a variety of antibodies. In one embodiment, the antibody specifically binds to a complex according to claim 1. In another embodiment, the antibody specifically binds to a complex according to claim 2. In another embodiment, the antibody specifically binds to a polypeptide, the polypeptide having an approximate molecular weight of 165,000 as determined by sodium dodecyl sulfate-polyacrylamide gel electrophoresis, and specifically binds to a complex according to claim 1. In another embodiment, the antibody specifically binds to a polypeptide, the polypeptide having an approximate molecular weight of 43,000 as determined by sodium dodecyl sulfate-polyacrylamide gel electrophoresis, and specifically binds to a complex according to claim 1. In another embodiment, the antibody specifically binds to a polypeptide, the polypeptide having an approximate molecular weight of 55,000 as determined by sodium dodecyl sulfate-polyacrylamide gel electrophoresis, and specifically binds to a complex according to claim 1. In another embodiment, the antibody specifically binds to a polypeptide, the polypeptide having an approximate molecular weight of 82,000 as determined by sodium dodecyl sulfate-polyacrylamide gel electrophoresis, and specifically binds to a complex according to claim 1. In another embodiment, the antibody specifically binds to a polypeptide, the polypeptide having an approximate molecular weight of 98,000 as determined by sodium dodecyl sulfate-polyacrylamide gel electrophoresis, and specifically binds to a complex according to claim 1.

Another aspect of the present invention provides methods for determining the presence or amount of a polypeptide component of a complex according to claim 1 or 2. Embodiments include use of an antibody described above in a method comprising the steps of: (a) isolating a urine sample from a warm-blooded animal; (b) incubating the sample with the antibody under conditions and for a time sufficient to allow immunocomplexes to form between the polypeptide and the antibody; and (c) detecting the presence or amount of the immunocomplexes, thereby determining the presence or amount of the polypeptide.

Another aspect of the present invention provides methods for determining the presence or amount of a complex according to claim 1. In one embodiment, the method comprises the steps of: (a) isolating a urine sample from a warm-blooded animal; and (b) detecting the presence or amount of the complex in the sample.

In another embodiment, the method comprises the steps of: (a) isolating a urine sample from a warm-blooded animal; and (b) detecting the presence or amount of the complex in the sample by immunological means.

In yet another embodiment, the method comprises the steps of: (a) isolating a urine sample from a warm-blooded animal; (b) incubating the sample with an antibody that specifically binds to a complex according to claim 1 under conditions and for a time sufficient to allow immunocomplexes to form between the complex and the antibody; and (c) detecting the presence or amount of the immunocomplexes, thereby determining the presence or amount of the complex in the sample.

Another aspect of the present invention provides methods for determining the presence or amount of a complex according to claim 2. In one embodiment, the method comprises the steps of: (a) isolating a urine sample from a warm-blooded animal; and (b) detecting the presence or amount of the complex in the sample.

In another embodiment, the method comprises the steps of: (a) isolating a urine sample from a warm-blooded animal; and (b) detecting the presence or amount of the complex in the sample by immunological means.

In yet another embodiment, the method comprises the steps of: (a) isolating a urine sample from a warm-blooded animal; (b) incubating the sample with an antibody that specifically binds to a complex according to claim 2 under conditions and for a time sufficient to allow immunocomplexes to form between the complex and the antibody; and (c) detecting the presence or amount of the immunocomplexes, thereby determining the presence or amount of the complex in the sample.

Another aspect of the present invention provides methods for the detection of metastatic bladder cancer. In one embodiment, the method comprises the steps of: (a) isolating a urine sample from a warm-blooded animal suspected of possessing a bladder tumor; (b) incubating the sample with an antibody that specifically binds to a complex according to claim 1 under conditions and for a time sufficient to allow immunocomplexes to form between the antibody and the complex; and (c) detecting the presence or absence of the immunocomplexes, thereby determining the presence or absence of the bladder cancer.

Another aspect of the present invention provides methods for the detection of a bladder epithelial disorder. In one embodiment, the method comprises the steps of: (a) isolating a urine sample from a warm-blooded animal suspected of possessing a bladder epithelial disorder; (b) incubating the sample with an antibody that specifically binds to a complex according to claim 2 under conditions and for a time sufficient to allow immunocomplexes to form between the antibody and the complex; and (c) detecting the presence or absence of the immunocomplexes, thereby determining the presence or absence of a bladder epithelial disorder.

In related aspects of the present invention, methods are provided for determining the presence or amount of complexes, which include basement membrane components, from a variety of biological samples. Such biological samples include cervical secretions, bronchial aspirates, sputum, feces and serum. The methods comprise the steps of: (a) isolating a desired biological sample from a warm-blooded animal; and (b) detecting the presence or amount of the complex in the sample.

Other aspects of the invention will become evident upon reference the following detailed description and attached drawings.

DETAILED DESCRIPTION OF THE INVENTION

Figure 1:
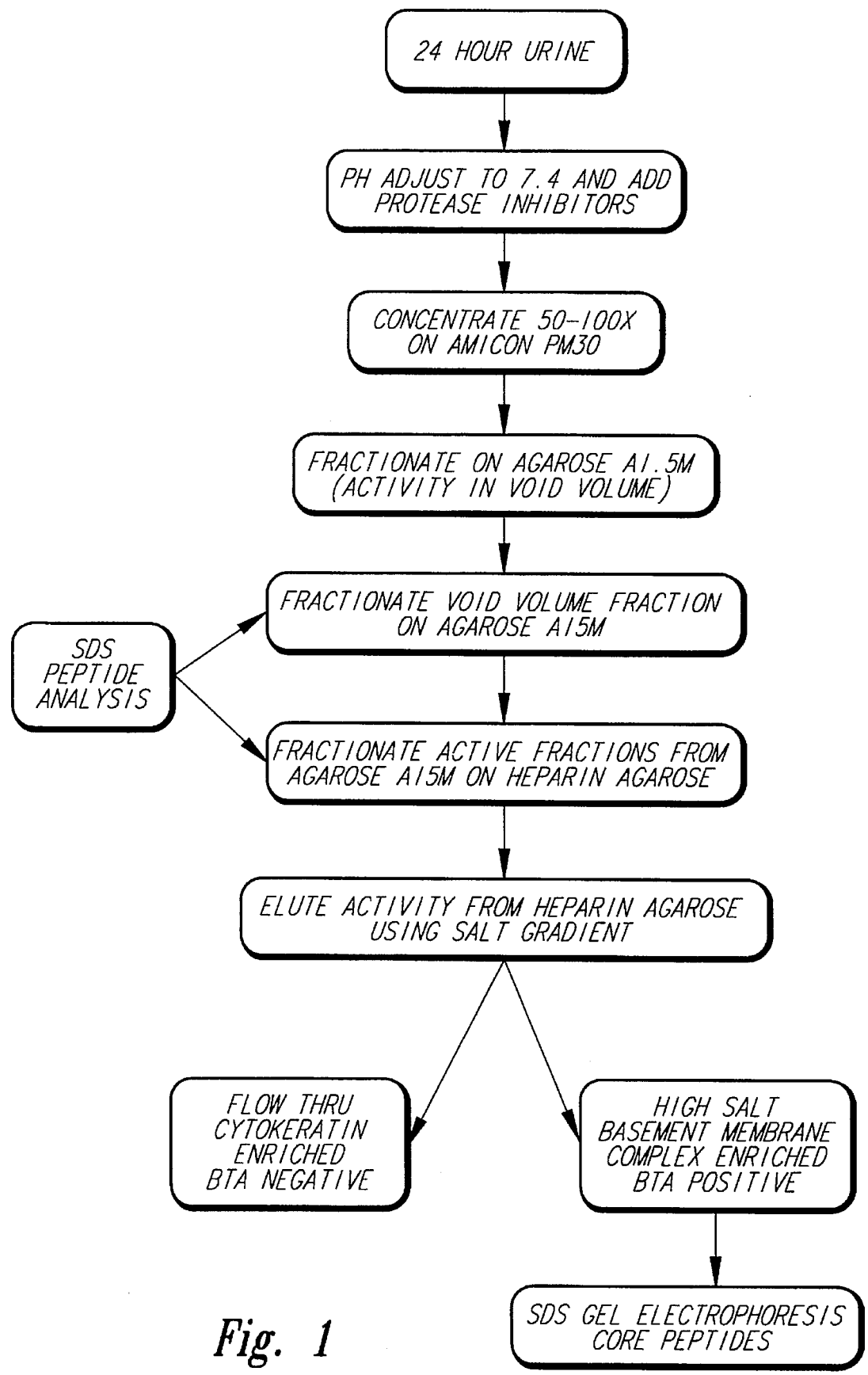
FIG. 1 is a flow chart for the purification of bladder tumor analyte ("BTA") complexes from urine of bladder cancer patients.

As noted above the present invention provides isolated complexes (which include basement membrane components), antibodies to such complexes or polypeptide constituents thereof, methods for detecting such complexes or constituents, and methods for the detection of diseases that result in the release of such complexes. Basement membranes (also referred to as basal lamina) are extracellular matrices separating organ parenchymal cells from connective tissue mesenchyme. Normally, parenchymal cells and stroma cells remain oriented on their respective side of the basement membrane, even during organ development and tissue repair. A number of diseases are apparently capable of disrupting basement membranes. The basement membrane is comprised of at least several identified proteins and peptide derivatives, including several specific types of collagen (e.g., Type IV and Type V), laminin, various types of cell adhesion molecules (CAMs), proteoglycans, and fibronectin.

Within the present invention, complexes which include basement membrane components have been found to survive in detectable concentrations in the biological samples of warm-blooded animals, including humans, possessing a disease which disrupts epithelial tissue. The basement membrane components in the complexes may be intact molecules, fragments thereof, or combinations of fragments and intact molecules. As disclosed in the present invention, complexes are indicative of a variety of diseases and are detectable in a variety of samples, with or without purification of such complexes. For example, complexes are associated with invasive cancers. Invasive cancers include cervical, urogenital (e.g., bladder and prostate), lung, colorectal, and head and neck cancers. Complexes are also associated with epithelial disorders (i.e., non-invasive or pre-invasive cancers and disorders unrelated to cancer) including epithelial inflammations, collagen degenerative diseases, and hepatitis. Epithelial inflammations include those which result from biopsies or deposits (e.g., "stones" in the bladder).

Representative types of biological samples include urine, cervical secretions, bronchial aspirates (including bronchial washings), sputum, saliva, feces, serum, synovial and cerebrospinal fluid. The type of biological sample in which complexes accumulate is dependent chiefly on the location of the particular disease. For example, urine is preferred for the detection of invasive urogenital cancers and urogenital epithelial disorders. Cervical secretions are preferred for the detection of invasive cervical cancers and cervical epithelial disorders. Bronchial aspirates and sputum are preferred for the detection of invasive lung cancers and lung epithelial disorders. Knowledge of the site from which a bronchial aspirate is taken further permits one to identify the location of a disease within a lung. Saliva is preferred for head and neck cancers. Feces are preferred for invasive colorectal cancers and colorectal epithelial disorders. Cerebrospinal fluid is preferred for brain cancers. It would be evident to those of ordinary skill in the art how to associate other biological samples with a particular disease location. Alternatively, serum may be used for the detection of complexes as a "pan" marker (i.e., a general screening technique) from which follow-up tests would be recommended to identify the particular disease.

Complexes from a biological sample may be isolated in substantial pure form. Briefly, for example, a sample may be fractionated by gel filtration and purified on heparin agarose or other anion or cation exchange media or by electroelution of specific polypeptides from polyacrylamide gels. A representative example of the purification of complexes is the isolation from a urine sample, as summarized in FIG. 1. It will be appreciated by those of ordinary skill in the art that complexes from other samples may be isolated in a similar manner.

Following isolation of complexes, the polypeptide constituents may be identified. Typically, polypeptides are resolved by separation (e.g., by gel electrophoresis) under denaturing conditions (e.g., sodium dodecyl sulfate). Approximate molecular weights of polypeptides are assigned by comparison to polypeptides of known molecular weights. For example, complexes from urine of patients with low grade non-invasive transitional cell carcinoma ("TCC") of the bladder contain predominantly two high molecular weight polypeptides with approximate molecular weights of 245,000 ("245k") and 190,000 ("190k"). For complexes from patients with low grade invasive TCC, the predominant polypeptides shift from molecular weights of about 245k and 190k to molecular weights of about 165k, 140k and 125k. For complexes from patients with high grade invasive TCC, the predominant polypeptides shift from molecular weights of about 165k, 140k and 125k to molecular weights of about 98k, 82k, 74k, 55k, 43k, 35k, 26k and 16k. All the foregoing approximate weights were determined on sodium dodecyl sulfate-polyacrylamide gel electrophoresis ("SDS-PAGE") by comparison to electrophoresis of polypeptide standards having known molecular weights.

Isolated complexes or individual polypeptide constituents are used to produce antibodies that specifically bind to an isolated complex, individual polypeptide, or both. Antibodies that specifically bind are those with an affinity of about $10^6$ liters/mol or greater. Either polyclonal antibodies or monoclonal antibodies may be generated. Polyclonal antibodies may be produced by immunization of an animal and subsequent collection of its sera. It is generally preferred to follow the initial immunization with one or more booster immunizations prior to sera collection. Monoclonal antibodies are generally produced by the method of Kohler and Milstein (*Nature* 256:495–497, 1975; *Eur. J. Immunol.* 6:511–519, 1976). Briefly, the lymph nodes and/or spleens of an animal injected with a basement membrane fragment or complex of fragments are fused with myeloma cells to form hybrid cell lines ("hybridomas" or "clones"). Each hybridoma secretes a single type of immunoglobulin specific for the fragment or liagment complex and, like the myeloma cells, has the potential for indefinite cell division.

A purified complex or polypeptide therefrom ("immunogen") is used for the immunization. Preferably, the animals are immunized with at least 100 ng each of the immunogen, most preferably greater than 500 ng each. For immunization, the immunogen may be adsorbed to a solid phase matrix, preferably to nitrocellulose paper. The paper is then introduced into the animal. Techniques for introduction of the adsorbed antigen preparation include implantation (U.S. Pat. No. 4,689,220) or solubilization of the solid phase and injection of the solubilized material (Knudsen, *Anal. Biochem.* 147:285–288, 1985). The solid phase matrix may be solubilized in an appropriate organic solvent (e.g., DMSO) and either mixed with adjuvant or saline, or injected directly.

Alternatively, the immunogen may be injected in the absence of a solid matrix and/or adjuvant. Injection or implantation may be intraperitoneal, intra-foot pad, subcutaneous, intramuscular or intravenous, but preferably intraperitoneal. The animals may also be injected with antigen complexed with adjuvant, such as Freund's adjuvant. Single or multiple booster immunizations are used. Between one and seven days prior to the fusion date, preferably on days one through four, intravenous injections of the appropriate immunogen may be given daily.

Between one and seven days, preferably four days, after the administration of the final booster immunization, spleens or portions thereof are harvested from the immunized animals. At this time, the lymph nodes may also be harvested and included in the cell preparation. The harvested organs are minced using techniques which disrupt the structure of the organ, but which are not detrimental to the lymphocytes. The organs are preferably minced with scissors, passed through a mesh screen and mixed with growth medium to enrich the preparation for lymphocytes. The minced and strained tissue is harvested by centrifugation, then mixed with growth medium to form a cell suspension. The red blood cells may be lysed by adding a hypotonic or hypertonic solution to the cell suspension. A preferred method for cell lysis is to add distilled water to the suspensions and quickly return the suspensions to an isotonic state with a hypertonic sodium chloride solution. Any remaining tissue may be removed by filtration through gauze.

The harvested cell suspension is then mixed with a myeloma cell line, preferably one which is syngeneic with the immunized animal. Myeloma cell lines from various species are widely available through, for example, American Type Culture Collection, Rockville, Md. Myeloma cell lines commonly used include P3X63Ag8 (ATCC TIB 9), SP2/0-Ag14 (ATCC CRL 1581), FO (ATCC CRL 1646) and 210-RCY-Ag1 (Galfre et al., *Nature* 277:131, 1979). A preferred cell line is P3/NS1/1-Ag4-1 hereinafter referred to as NS-1 (ATCC TIB 18). The NS-1 cells are preferably tested to determine the cloning efficiency of the strain. This may be accomplished by cloning out the NS-1 strain by limiting dilution and carrying out test fusions with the individual NS-1 clones to find candidates with the highest fusion efficiencies.

The myeloma cells are cultured in an appropriate mammalian cell growth medium, a variety of which are generally known in the art and available from commercial sources. Mammalian cell lines are routinely grown between 36° C. and 40° C. under conditions which maintain an optimal pH between 6.0 and 8.0, preferably about pH 7.2. pH may be maintained through the use of a variety of buffer systems known in the art. A preferred buffer system involves growing the cells in a bicarbonate buffer in a humidified incubator containing $CO_2$, preferably about 7% $CO_2$.

The fusion between the lymphocytes from the immunized animal and the myeloma cells may be carried out by a variety of methods described in the literature. These methods include the use of polyethylene glycol (PEG) (Brown et al., *J. Biol. Chem.* 255:4980–4983, 1980) and electrofusion (Zimmerman and Vienken, *J. Membrane Biol.* 67:165–182, 1982). An electrofusion generator is commercially available from Biotechnologies and Experimental Research, Inc., San Diego, Calif.

Following the fusion, the cells are plated onto multi-well culture plates, preferably 96-well plates. A reagent which selectively allows for the growth of the fused myeloma cells over the unfused cells is added to the culture medium. A preferred selection technique uses HAT (hypoxanthine, aminopterin, thymidine) selection. Other selection techhniques may also be used depending on the myeloma cell line chosen.

Alternative methods of producing monoclonal antibodies utilize in vitro immunization techniques. Lymphocytes may be harvested from lymphoid organs, such as spleen or lymph nodes, or from whole blood as peripheral blood lymphocytes. The lymphocytes are put into culture in the presence of the appropriate immunogen. Other immunostimulatory polypeptides will be added to the culture medium concurrently. At various times following the culturing of the lymphocytes in vitro, the lymphocytes are harvested and fused with a myeloma cell line as described above.

Other techniques liar producing and maintaining antibody secreting lymphocyte cell lines in culture include viral transfection of the lymphocyte to produce a transformed cell line which will continue to grow in culture. Epstein barr virus (EBV) has been used for this technique. EBV transformed cells do not require fusion with a myeloma cell to allow continued growth in culture.

Thymocytes may be used as a feeder layer to condition the medium for the fused cells. Alternatively, peritoneal macrophages or non-immune spleen cells may be used as a feeder layer. Another alternative is to use conditioned medium from thymocytes or macrophages. Thymocytes may be prepared from juvenile mice less than 8 weeks old. The thymus glands are harvested and minced using techniques which disrupt the thymus gland but are not detrimental to the thymocytes. This procedure is preferably carried out using scissors to mince the tissue, followed by passage of the tissue through a mesh screen. The minced and strained cell material is then harvested by centrifugation. Cell suspensions are made using growth medium. Any remaining connective tissue may be removed by filtration through gauze.

At an appropriate time following the day the cells are fused, the fused cells (hybridomas) are then analyzed for the production of antibody against the antigen of choice. This "screening" can be done by a wide variety of techniques, including Western blot, ELISA, immunoprecipitation, affect on biological activity assays and immunocytochemical staining. These techniques and others are well described in the literature. (See, for example, J. G. R. Hurrell (ed.), *Monoclonal Hybridoma Antibodies: Techniques and Applications*, CRC Press Inc., Boca Raton, Fla., 1982.) Introduction of a screening procedure permits further definition of antibodies of useful reactivity. For example, complexes purified from a biological sample of a patient with a particular disease, such as cervical cancer, may be used in any of the above-named techniques to define antibodies which react, for example, to determinants which are common to patients with the disease.

Hybridomas which secrete antibodies of interest are maintained in culture. The cells are expanded in culture and at the same time may be cloned in such a manner as to obtain colonies originating from single cells. This provides for the monoclonal nature of the antibodies obtained from the hybridomas. A wide variety of techniques exist for cloning cells, including limiting dilution, soft agar cloning and fluorescence-activated cell sorting.

Once clones of cells are obtained, they are re-assayed for the production of the antibody of interest. These cells are then expanded in culture to allow for the production of larger amounts of the antibody. Methods for expansion of the cells include maintaining the cells in culture, placement of the cells in a bioreactor or other type of large-scale cell culture environment, or culturing the cells using various agar or gelatin carrier matrices. Antibodies are then isolated from the cell culture media.

A preferred method of producing large amounts of antibodies involves growing the hybridoma cells in the peritoneal cavity of syngeneic mice, thereby producing ascites fluid. The hybridomas are preferably isolated from the culture media by centrifugation and washed with an isoosmotic solution, preferably phosphate buffered saline. The cells are then resuspended in an isoosmotic solution and injected into the peritoneal cavity of an appropriate host animal, preferably a mouse, and allowed to grow within the host animal. The host animal may receive a pre-injection of pristane (2,6,10,14-tetramethylpentadecane) prior to the injection of the hybridoma cells, preferably seven to thirty days prior to the introduction of the hybridomas. Following growth of the cells in the peritoneal cavity, ascites fluid, containing the antibody of interest, is collected.

Antibodies may be purified from conditioned media or ascites fluid by a variety of methods known in the art. These methods include ammonium sulfate precipitation, ion exchange chromatography (see Hurrell, ibid.) and high pressure liquid chromatography using a hydroxylapatite support (Stanker et al., *J. Immunol. Methods* 76:157, 1985). A preferred method for purifying antibodies from conditioned media or ascites fluid utilizes a commercially available Protein A-Sepharose CL-4B column or Protein G Sepharose (Pharmacia, Piscataway, N.J.; Sigma, St. Louis, Mo.) or ABX mixed ion exchange resin (J T Baker, Phillipsburg, N.J.). Antibodies may be purified with these columns using conditions suggested by the manufacturer. Typically, the conditioned medium or ascites fluid is dialyzed into phosphate buffered saline to give a pH of 7.5–8 and applied to the a protein-A sepharose column. The antibodies are eluted by lowering the pH in a stepwise fashion with 100 mM sodium citrate buffers of pH 7, 6, 4.5 and 3.5, respectively. Antibody-containing elements are immediately adjusted to pH 7.4, preferably using a saturated trisodium phosphate solution or concentrated Tris buffer. Alternatively, ABX, a mixed mode ion exchanger is equilibrated with 25 mM MES buffer, pH 5.6, (2-(n-Morpholino) ethane sulfonic acid (Sigma Chem. Co., St. Louis, Mo.). Concentrated conditioned media or ascites is diluted 1:3 in 100 mM MES buffer, pH 5.5, and the pH adjusted to that of the column equilibration buffer. Sample is applied to the column and eluted in equilibration buffer. Bound antibody is eluted with the 25 mM MES buffer, pH 5.6, containing 10% (v/v) of a 25 mM potassium phosphate containing 500 mM ammonium sulfate, pH 5.6, buffer, this is followed by a linear gradient from 10%–100% (v/v) of the 25 mM potassium phosphate buffer containing 500 mM ammonium sulfate, pH 5.6.

The presence or amount of a complex or one or more polypeptide components of a complex may be determined in a variety of ways, including non-immunological and immunological. Non-immunological methodologies include the use of protein stains such as Coomassie blue or silver stains. In a preferred embodiment, a sample suspected of containing a complex is subjected to SDS-PAGE and identified using a protein stain. Other non-immunological methodologies include the use of radioisotopes and the like as reporter groups. Such methods are amenable to quantification where it is desired to determine the amount.

Alternatively, the presence or amount of a complex or polypeptide component may be detected by immunological means. As used herein, the term "antibody" includes both polyclonal and monoclonal antibodies; and may be an intact molecule, a fragment thereof, or a functional equivalent thereof; and may be genetically engineered. Examples of antibody fragments include F(ab')$_2$, Fab', Fab and Fv. Detection may be, for example, by Western blot analysis utilizing immobilized complexes or components thereof on nitrocellulose, or Immobilon or similar matrix in conjunction with specific antibodies to the complexes or to individual components of the complexes. Detection can also be achieved by immunoassay. In one embodiment, a complex or polypeptide is isolated from a sample and contacted with an appropriate detection antibody. Complexes may be isolated by capture on a solid support (e.g., heparin agarose or polystyrene or heparin coated on polystyrene) or with a "capture" antibody prior to or simultaneous with a "detection" antibody. In another embodiment, immunocomplexes are formed between an antibody and a complex, without prior purification of the complex. Incubation of a sample with an antibody is under conditions and for a time sufficient to allow immunocomplexes to form. Detection of complexes or polypeptide constituents by immunological means is also amenable to quantification where it is desired to determine the amount of a particular complex or polypeptide constituent.

Detection of one or more immunocomplexes formed between a complex or polypeptide component and an antibody specific for the complex or polypeptide may be accomplished by a variety of known techniques, including radioimmunoassays (RIA) and enzyme linked immunosorbent assays (ELISA).

The immunoassays known in the art include the double monoclonal antibody sandwich immunoassay technique of David et al. (U.S. Pat. No. 4,376,110); monoclonal-polyclonal antibody sandwich assays (Wide et al., in Kirkham and Hunter (eds.), *Radioimmunoassay Methods*, E. and S. Livingstone, Edinburgh, 1970); the "western blot" method of Gordon et al. (U.S. Pat. No. 4,452,901); immunoprecipitation of labeled ligand (Brown et al., *J, Biol. Chem.* 255:4980–4983, 1980); enzyme-linked immunosorbant assays as described by, for example, Raines and Ross (*J. Biol. Chem.* 257:5154–5160, 1982); immunocytochemical techniques, including the use of fluorochromes (Brooks et al., *Clin. Exp. Immunol.* 39: 477, 1980); and neutralization of activity (Bowen-Pope et al., *Proc. Natl. Acad. Sci. U.S.A.* 81:2396–2400, 1984), all of which are hereby incorporated by reference. In addition to the immunoassays described above, a number of other immunoassays are available, including those described in U.S. Pat. Nos.: 3,817,827; 3,850,752; 3,901,654; 3,935,074; 3,984,533; 3,996,345; 4,034,074; and 4,098,876, all of which are herein incorporated by reference.

For detection purposes, the antibodies may either be labeled or unlabeled. When unlabeled, the antibodies find use in agglutination assays. In addition, unlabeled antibodies can be used in combination with other labeled antibodies (second antibodies) that are reactive with the antibody, such as antibodies specific for immunoglobulin. Alternatively, the antibodies can be directly labeled. Where they are labeled, the reporter group can include radioisotopes, fluorophores, enzymes, luminescers, or dye particles. These and other labels are well known in the art and are described, for example, in the following U.S. Pat. Nos.: 3,766,162; 3,791,932; 3,817,837; 3,996,345; and 4,233,402.

Typically in an ELISA assay the target antigen or immobilized capture antibody is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1%–5.0% by weight) of protein, such as BSA, NGS, or BLOTTO. After incubating for a sufficient length of time to allow specific binding to occur, the well is washed to remove unbound protein and then incubated with an anti-mouse immunoglobulin antibody labeled with a reporter group. The reporter group can be chosen from a variety of enzymes, including horseradish peroxidase, beta-galactosidase, alkaline phosphatase, and glucose oxidase. Sufficient time is allowed for specific binding to occur, the well is again washed to remove unbound conjugate, and the substrate for the enzyme is added. Color is allowed to develop and the optical density of the contents of the well is determined visually or instrumentally.

In one preferred embodiment of the present invention, a reporter group is bound to the antibody. The step of detecting an immunocomplex involves removing substantially any unbound antibody and then detecting the presence or absence of the reporter group.

In another preferred embodiment, a reporter group is bound to a second antibody capable of binding to the antibody specific for a complex of one or more basement membrane components. The step of detecting an immunocomplex involves (a) removing substantially any unbound antibody, (b) adding the second antibody, (c) removing substantially any unbound second antibody and then (d) detecting the presence or absence of the reporter group. Where the antibody specific for the fragment is derived from a mouse, the second antibody is an anti-murine antibody.

In a third preferred embodiment for detecting an immunocomplex, a reporter group is bound to a molecule capable of binding to the immunocomplex. The step of detecting involves (a) adding the molecule, (b) removing substantially any unbound molecule, and then (c) detecting the presence or absence of the reporter group. An example of a molecule capable of binding to the immunocomplex is protein A.

It will be evident to one skilled in the art that a variety of methods for detecting the immunocomplex may be employed within the present invention. Reporter groups suitable for use in any of the methods include radioisotopes, fluorophores, enzymes, luminescers, and dye particles.

As disclosed herein, the polypeptide composition of a complex is related to whether the disease is an epithelial disorder (including superficial cancers) or an invasive cancer. By detecting the presence or absence of a particular complex, the presence or absence of a particular disease may be determined. For example, the presence of a bladder epithelial disorder (e.g., superficial cancer) is indicated by the presence in urine of complexes containing polypeptides with approximate molecular weights of 245k and 190k. Similarly, where complexes containing polypeptides with approximate molecular weights of 165k, 140k and 125k are detected in urine, the presence of invasive bladder cancer is indicated. These polypeptides are absent in urine of normal individuals. Complexes in a sample may be detected by a variety of non-immunological or immunological means as described above.

As also disclosed herein, the grade of a tumor (i.e., its invasive potential) is related to the polypeptide composition of the complexes in the sample. For example, complexes from patients with low grade invasive TCC of the bladder contain predominantly polypeptides with molecular weights of about 165k, 140k and 125k. Conversely, complexes from patients with high grade invasive TCC of the bladder have a polypeptide profile which has shifted from predominant molecular weights of about 165k, 140k and 125k, to molecular weights of about 98k, 82k, 74k, 55k, 43k, 35k, 26k, and 16k. In one embodiment, the grade of a cancer may be determined by measuring the amount of a complex and its polypeptide composition, e.g., by immunological or non-immunological methods as described above.

In another embodiment, the grade of a cancer may be determined by comparing the amount of one polypeptide to the amount of another polypeptide. For example, for determining the grade of a bladder tumor, the amount of a first polypeptide having an approximate molecular weight of either 165k, 140k, or 125k is compared to the amount of a second polypeptide having an approximate molecular weight of either 98k, 82k, 74k, 55k, 43k, 35k, 26k, or 16k. Where the ratio of the amount of the first polypeptide exceeds the amount of the second polypeptide, the grade of the invasive cancer is low. Conversely, where the ratio of the amount of the second polypeptide exceeds the amount of the first polypeptide, the grade of the invasive cancer is high. In any embodiment for determining the grade of an invasive tumor, the presence or amount of a complex, its polypeptide composition, and/or one or more individual polypeptides may be detected by a variety of non-immunological or immunological means, including those described above.

As noted above, the present invention also provides a physicochemical method for the detection of a disease that results in the release of fragments, intact molecules and/or complexes of one or more basement membrane components. This method is based upon the ability of molecules ("analytes") released by a disease into biological fluids to agglutinate a suspension of microparticles. In the case of cancers, for example, the analytes represent molecules which are released into a biological fluid as result of the metastatic process or the growth of a tumor and which agglutinate a suspension of microparticles.

The physicochemical method generally comprises contacting a biological fluid with a suspension of microparticles which agglutinate in the presence of liagments, intact molecules and/or complexes of basement membrane components. Subsequently, the presence or absence of agglutination of the suspension of microparticles is detected, thereby allowing the determination of the presence or absence of the disease. Representative diseases and biological fluids include those described above for the immunological method.

Microparticles suitable for use in this method include plastic latex, e.g., latex beads. Such a suspension of microscopic plastic particles is commonly prepared from polystyrene and derivatives thereof. The plastic may be in an underivatized form or in the form of derivatives, such as carboxylated or aminated. Typically, the microparticle has a diameter from about 0.01 to 5 microns, with about 0.25 microns preferred. It is advantageous to treat the suspensions of microparticles with one or more agents, such as bovine serum albumin, to block sites upon the surface of the particles which are available for nonspecific interactions.

The suspension of microparticles agglutinates in the presence of a biological fluid from a patient with a disease that results in the release of fragments, intact molecules and/or complexes of one or more basement membrane components. This agglutination reaction permits the detection of small amounts of basement membrane fragments, intact molecules or complexes in the presence of relatively large amounts of exogenous protein present in the biological fluid being tested. Thus, pretreatment of the biological fluid prior to testing is generally not required. In the case of biological fluids containing particulate contaminants, such as urine containing bacteria, cells, crystals, or other sediment, a brief centrifugation at low speeds sufficient to remove the particulate contaminants may be desirable, as is neutralizing the pH with buffer.

It will be evident to one skilled in the art that a variety of methods for detecting the presence or absence of agglutination of a suspension of microparticles may be employed within the present invention. For example, a simple slide agglutination technique, such as those used extensively with small particle agglutination techniques, is suitable. In this technique, an aliquot of the suspension of microparticles is mixed with an aliquot of the specimen being tested on the surface of a glass slide. The reactants are mixed by rotating the slide manually or on a mechanical rotator. At time intervals, the appearance of the mixed reactants is judged relative to the appearance of the mixed reactants is judged relative to the appearance of a positive and negative control, which consists of known analyte-containing and non-analyte-containing specimen material, respectively. If, when viewed either macroscopically or microscopically, the unknown specimen being tested has caused agglutination of the microparticles in excess of that apparent in the negative control, the presence of an analyte in the unknown is established.

Other methods of determining the extent of aggregation of a suspension may also be used (e.g., as described by Cohen & Benedek, U.S. Pat. No. 4,080,264; Kraemer, *Am. J. Med. Tech.*, Vol. 48, No. 8, 1982; Looney, *J. Clin. Immun.* 7:90–95, 1984; and Grange et al., *J. Immun. Meth.* 8:365–375, 1977). Briefly, these include systems which detect the increase in rate of sedimentation of particles due to aggregation. Sedimentation may be judged visually or with the help of instrumentation which will record the increased rate of sedimentation by virtue of optical or other properties of the suspension. The distinctive light scattering properties of aggregates versus nonaggregated micropar- ticles may be measured with a spectrophotometer or nephelometer set at any wavelength capable of measuring changes in these properties, e.g., 350, 660 or 700 nm.

The following examples are offered by way of illustration and not by way of limitation.

EXAMPLES

EXAMPLE 1

LATEX AGGLUTINATION ASSAYS FOR BASEMENT MEMBRANE COMPLEXES (BLADDER TUMOR ANALYTE, BTA) IN URINES OF BLADDER CANCER PATIENTS OF DIFFERENT STAGE AND GRADE

Latex agglutination assays for the detection of the bladder tumor analyte ("BTA") were performed in two different formats, a slide agglutination assay and a colored dipstick agglutination format. Both assays measure, using the same principle, the presence of BTA in urine which is formed and secreted into urine by transitional cell carcinomas of the bladder.

Latex reagent for use in the slide agglutination assay is prepared as follows. To 750 ml of 49% suspension of 0.25 micron diameter carboxylated polystyrene latex (Morton Thiokol, Morton Thiokol International, Chicago, Ill.) is added 2 ml of goat serum from a healthy unimmunized goat which has been diluted 1:10 in 0.85% saline. The mixture is placed in a 56° C. water bath for 60 minutes and stirred using a magnetic stirrer, or similar device, for 18–24 hours at room temperature. Seventy five ml of this stock latex suspension is diluted 1:40 with 2925 ml of 0.013M Glycine Buffer (pH 8.2 containing 0.1% sodium azide) containing 4 g of bovine serum albumin (BSA). This latex suspension is mixed for two hours using a magnetic stirrer or similar device. The suspension is then adjusted to an optical density of 0.31 OD (optical density standard) units at 700 nm, using distilled water as a blank, on a spectrophotometer to yield "Latex reagent". The addition of 12 mg of human gamma globulin (in 20 ml of 0.85% saline) prior to the 56° C. heat treatment step improves agglutinating activity.

Latex agglutination assays were performed by placing 50 µl of urine within a circle or well on a black serology or similar slide. Subsequently 50 µl of working "latex reagent" is placed on the urine sample. The mixture is stirred to the outer edge of the circle using a clean plastic stirrer, and rocked gently for 2 minutes. The slide is examined visually for agglutination of the latex particles. Improved assay performance was obtained by neutralizing urine samples with 10 µl of 1M Hepes buffer, pH 7.8, prior to adding latex reagent.

Latex reagent for use in the dipstick assay is prepared as described below. A stock latex was prepared by adding 12 mg of human IgG to 20 ml of saline solution and then adding this solution to 750 ml of 48% solution of 0.25 micron particles. Two ml of normal goat serum was mixed with 18 ml of normal saline and added to the latex suspension. The stock latex suspension was heated at 56° C. for 1 hour and mixed gently. The latex suspension was allowed to cool to 30° C. and 1.88 g of Brilliant Blue R dye was added and mixed for 18 hours at room temperature.

A working latex was prepared by adding 1 g of sodium azide, 1 gm of glycine, 1.5 g of bovine serum albumin, 30 ml of water soluble yellow dye and 105 ml of stock latex suspension to 3 liters of distilled water. The reagent was adjusted to pH 8.5 and mixed for 2 hours.

Latex agglutination dipstick assays for BTA detection in urine samples were performed by the following procedure. Urine samples (0.5 ml) were neutralized by the addition of 1 drop of 1M Hepes buffer, pH 7.8. Thirty five microliters of this sample was then mixed with 35 µl of the working latex reagent in a plastic well and allowed to react for approximately 30 seconds. Fiber glass dipsticks with con- trolled pore size glass were now added carefully to the well and the reaction mix allowed to migrate up the dipstick. Urine samples were considered to be positive for BTA if a distinct yellow above blue coloration is observed. A gradu- ally lightening green or green above diffuse blue is consid- ered a negative. BTA dipstick assays on column fractions do not use the Hepes neutralization.

Urine samples from patients being monitored for bladder cancer recurrence were tested using either of the above procedures and compared with voided urine cytology ("VUC") performed at the individual clinical sites. VUC is commonly used in the monitoring of bladder cancer patients, but suffers from low sensitivity in the detection of low grade tumors. Several examples where VUC and the latex agglu- tination assay were compared in a transitional cell carci- noma ("TCC") monitoring situation over a period of time are shown in Table 1 along with the biopsy data and the cystoscopic findings. In this data, initial studies were per- formed with the slide form of the assay. All subsequent data was performed with the dipstick assay.

TABLE 1

RELATIONSHIP OF BTA TO VUC, CYSTOCOPY AND BIOPSY IN SELECTED MONITORED PATIENTS

| CASE | MONTH | BTA | VUC | CYSTOCOPY | BIOPSY |
| --- | --- | --- | --- | --- | --- |
| 1 | 1 | − | — | NORMAL | NO |
|  | 6 | + | — | PIPILLARY TUMOR | NEGATIVE |
|  | 11 | + | SUSPICIOUS | PAPILLARY TUMOR | Ta GRADE II |
| 2* | 1 | + | ATYPICAL | INVASIVE TUMOR | T1 GRADE III |
|  | 7 | + | — | ERYTHEMA | NEGATIVE |

TABLE 1-continued

RELATIONSHIP OF BTA TO VUC, CYSTOCOPY AND BIOPSY IN SELECTED MONITORED PATIENTS

| CASE | MONTH | BTA | VUC | CYSTOCOPY | BIOPSY |
|---|---|---|---|---|---|
| | 9 | − | *On intravesical therapy | NEGATIVE | NEGATIVE |
| 3 | 1 | + | — | PAPILLARY TUMOR | Ta GRADE I |
| | 7 | + | REACT CHANGES | PAPILLARY TUMOR | NEGATIVE |
| | 8 | + | TUMOR | PAPILLARY TUMOR | NEGATIVE |
| 4 | 1 | − | — | NORMAL | NO |
| | 7 | + | UROTHELIAL CA | PAPILLARY TUMOR | Ta GRADE II/CIS |
| 5 | 1 | − | REACT CHANGES | ERYTHEMA | NO |
| | 6 | + | UROTHELIAL CA | NORMAL | NO |
| | 10 | + | UROTHELIAL CA | TUMOR | TCC |
| 6 | 1 | + | REACT CHANGES | NORMAL | NO |
| | 3 | + | UROTHELIAL CA | NORMAL | NO |
| | 7 | + | UROTHELIAL CA | ERYTHEMA | TCC |
| | 8 | + | UROTHELIAL CA | TUMOR | TCC |

The data indicates that the agglutination assay is capable of detecting complexes in the urine of monitored TCC patients prior to VUC and in some cases precedes diagnosis by cystoscopy. In addition, the reactivity in urine increases as the tumor progresses and decreases upon treatment as would be expected for an analyte representative of tumor burden.

The ability of the BTA slide agglutination assay to detect complexes in urines of different stages and grades of tumor is shown in Tables 2 and 3. The data indicate that the assay detects low grade tumors as well as high grade tumors, but that the detection rate increases with histological grade of the tumor.

TABLE 2

SENSITIVITY OF BTA DIPSTICK AND VUC FOR URINES OF TCC PATIENTS OF DIFFERENT HISTOLOGICAL GRADE

| GRADE | BTA | VUC |
|---|---|---|
| I | 11/19 | 2/19 |
| II | 5/8 | 2/8 |
| III | 12/16 | 10/16 |

Bladder tumors are typically designated as: superficial if papillary (Stage Ta), or surface tumors (Stage CIS), or invasive (Stage T1–T3) if penetrating the basal lamina and eventually the muscle and surrounding tissue. Procedures used in the treatment of bladder cancer are often based on the invasive nature of the tumor and it is therefore important to be able to monitor the types of tumor. The ability of the BTA dipstick test to detect these different types of tumor as compared to VUC in a population of patients being monitored for TCC recurrence is shown in Table 3.

TABLE 3

SENSITIVITY OF BTA DIPSTICK AND VUC FOR URINES PATIENTS WITH SUPERFICIAL AND INVASIVE TCC

| TUMOR STAGE | BTA | VUC |
|---|---|---|
| SUPERFICIAL (Ta-CIS) | 16/30 | 4/30 |
| INVASIVE (T1-T3) | 13/16 | 9/16 |

The data indicates the superiority of the BTA assay in detecting low grade superficial tumors as compared to VUC and supports its use as an adjunct test in monitoring tumor recurrence.

EXAMPLE 2

GEL FILTRATION OF 24 HOUR URINES FROM PATIENTS WITH DIFFERENT STAGES AND GRADE OF TCC

Twenty four hour voided urines collected from patients with transitional cell carcinoma (TCC) of the bladder and at different stage and grade of disease representative of superficial and invasive tumors, as well as normal urine pools were fractionated as described in the flow diagram shown in FIG. 1.

Figure 2A:
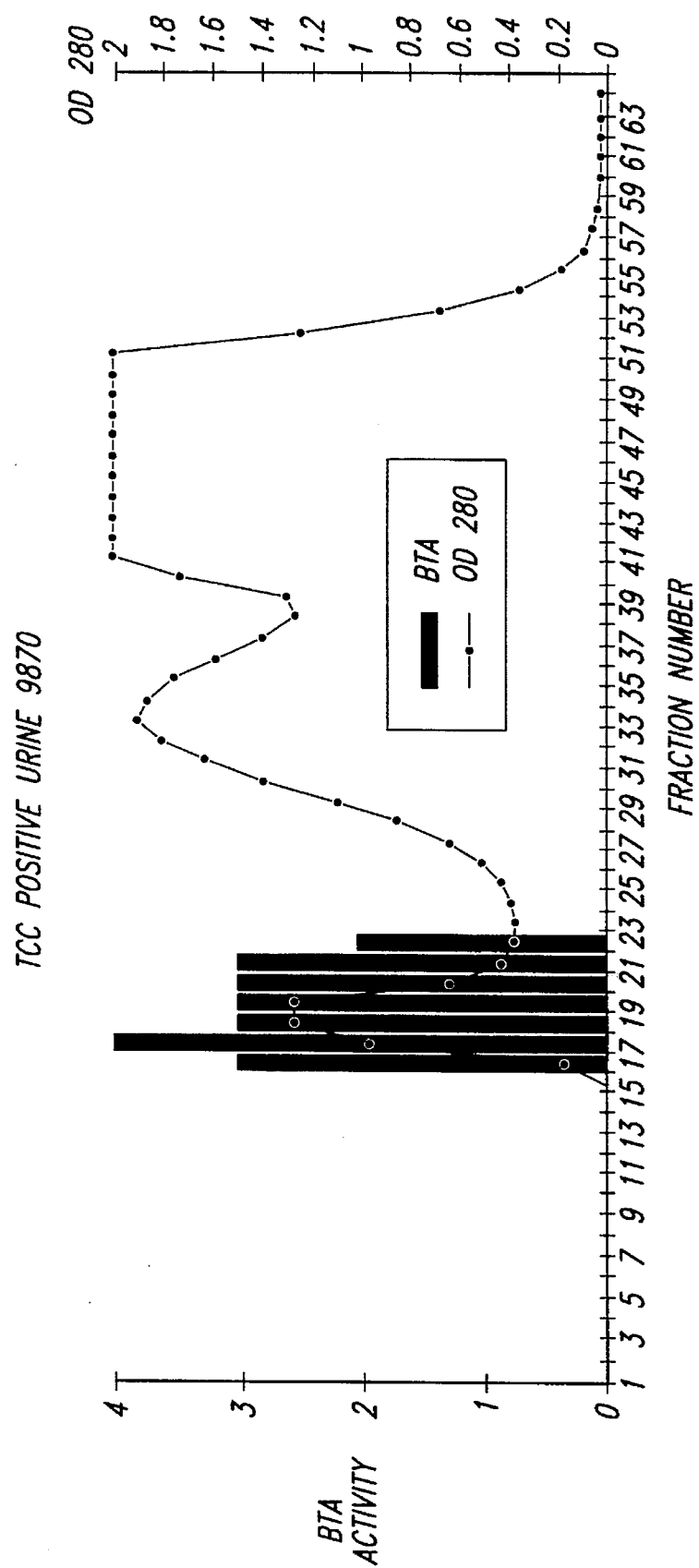
FIG. 2 graphically depicts A1.5M agarose gel filtration of a transitional cell carcinoma ("TCC") positive (Panel A) and negative urine (Panel B).
Figure 2B:
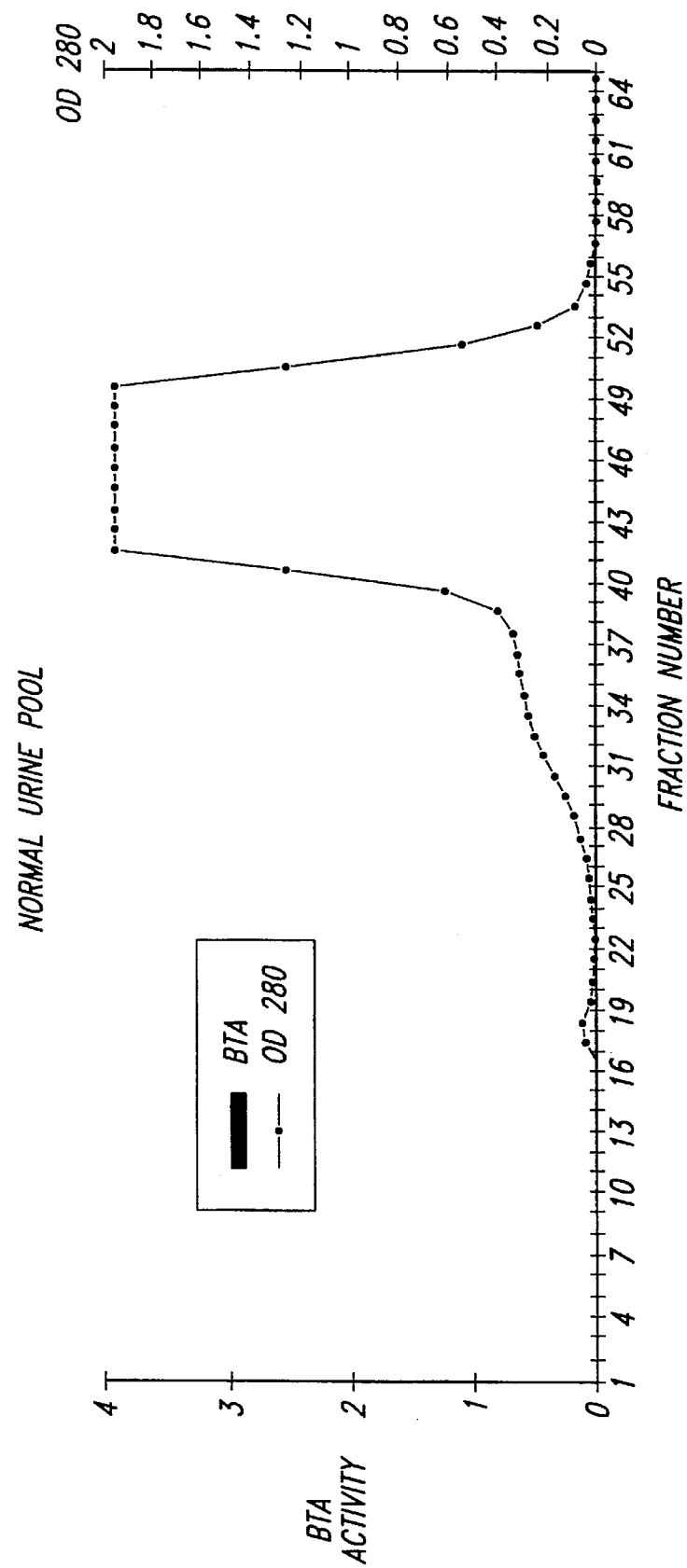
Figure 3A:
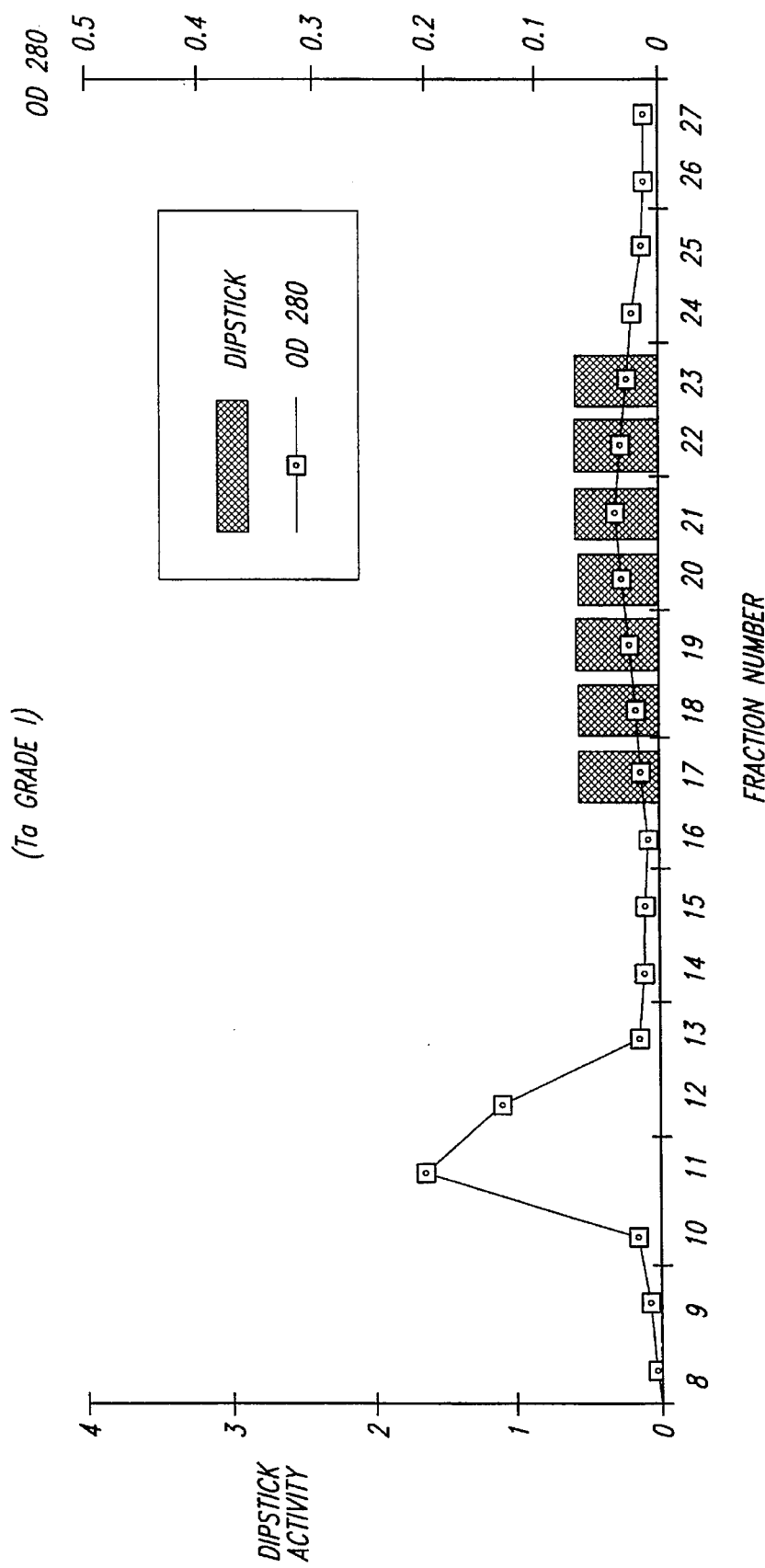
FIG. 3 graphically illustrates A15 agarose gel filtration of urines from bladder cancer patients with different stage and grade of TCC (Panels A–D).
Figure 3B:
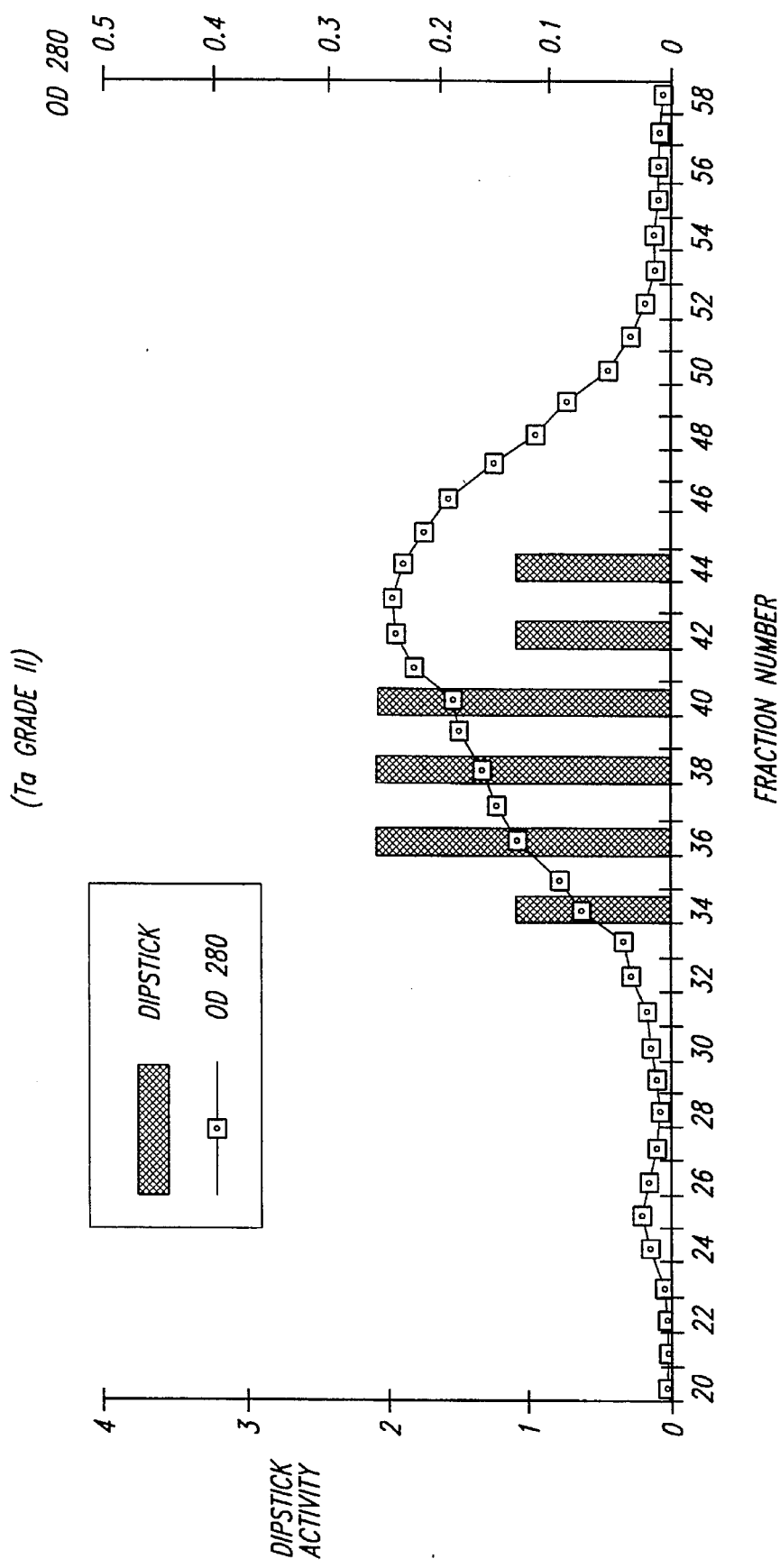
Figure 3C:
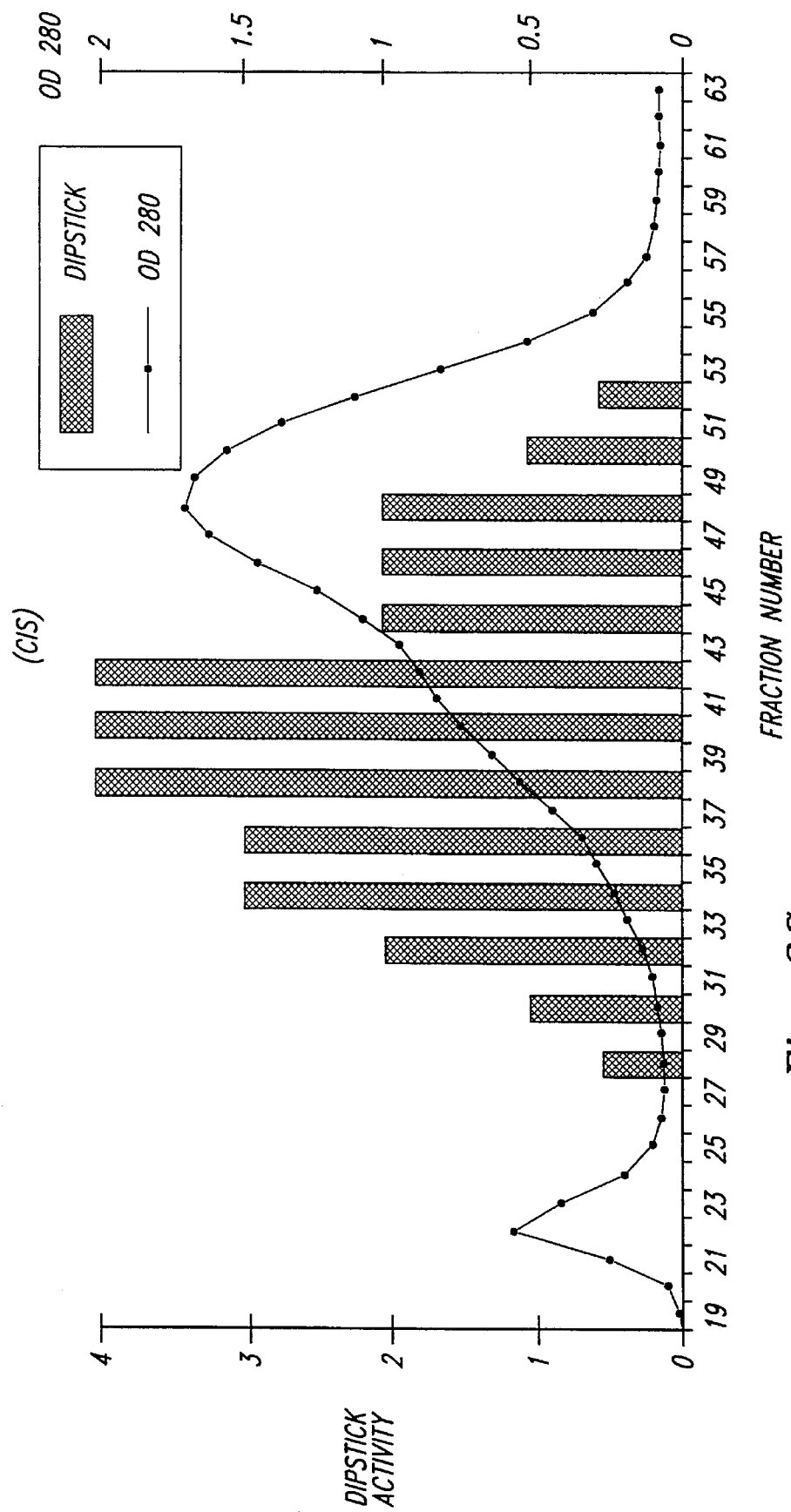
Figure 3D:
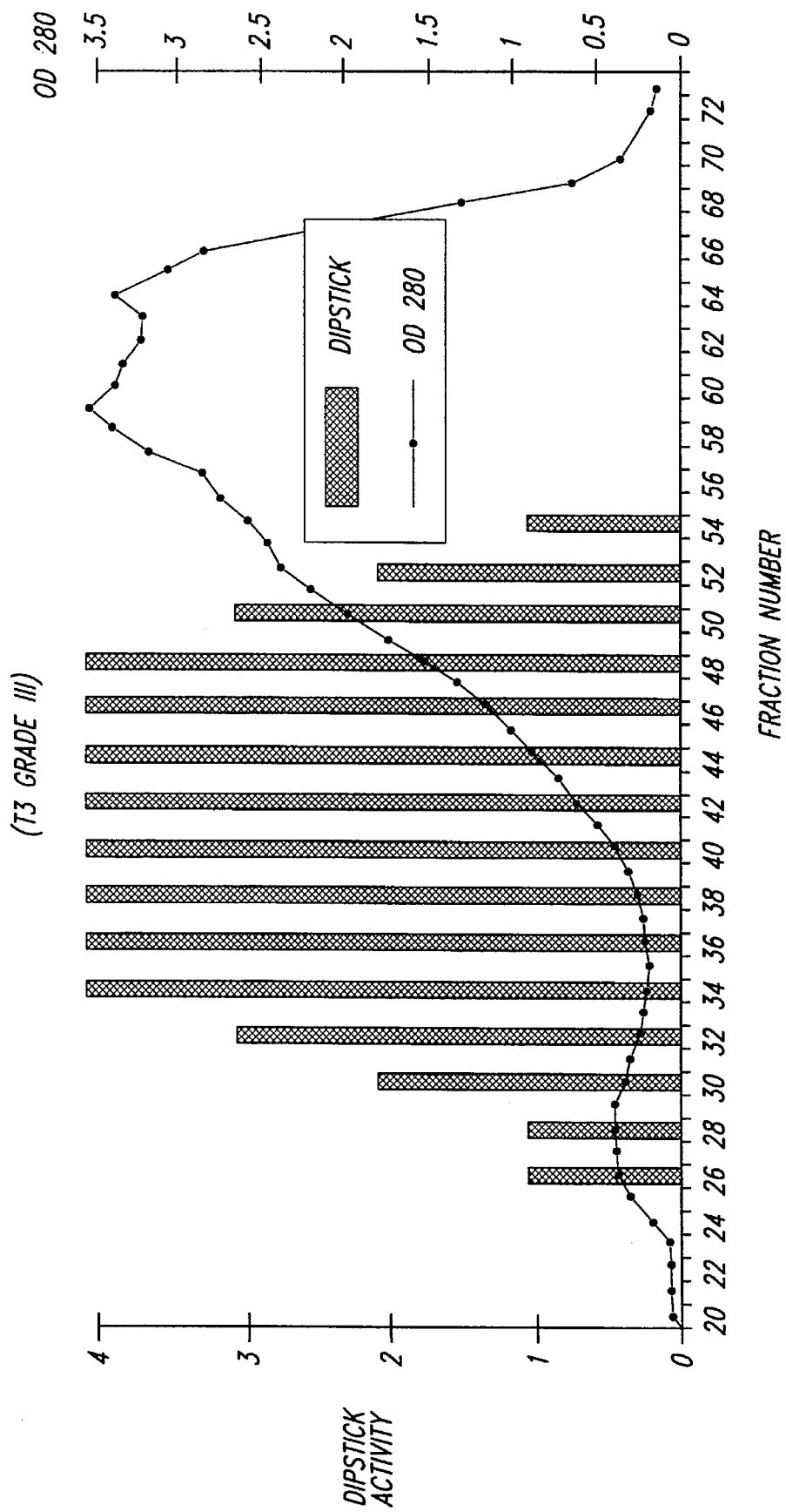
Figure 4A:
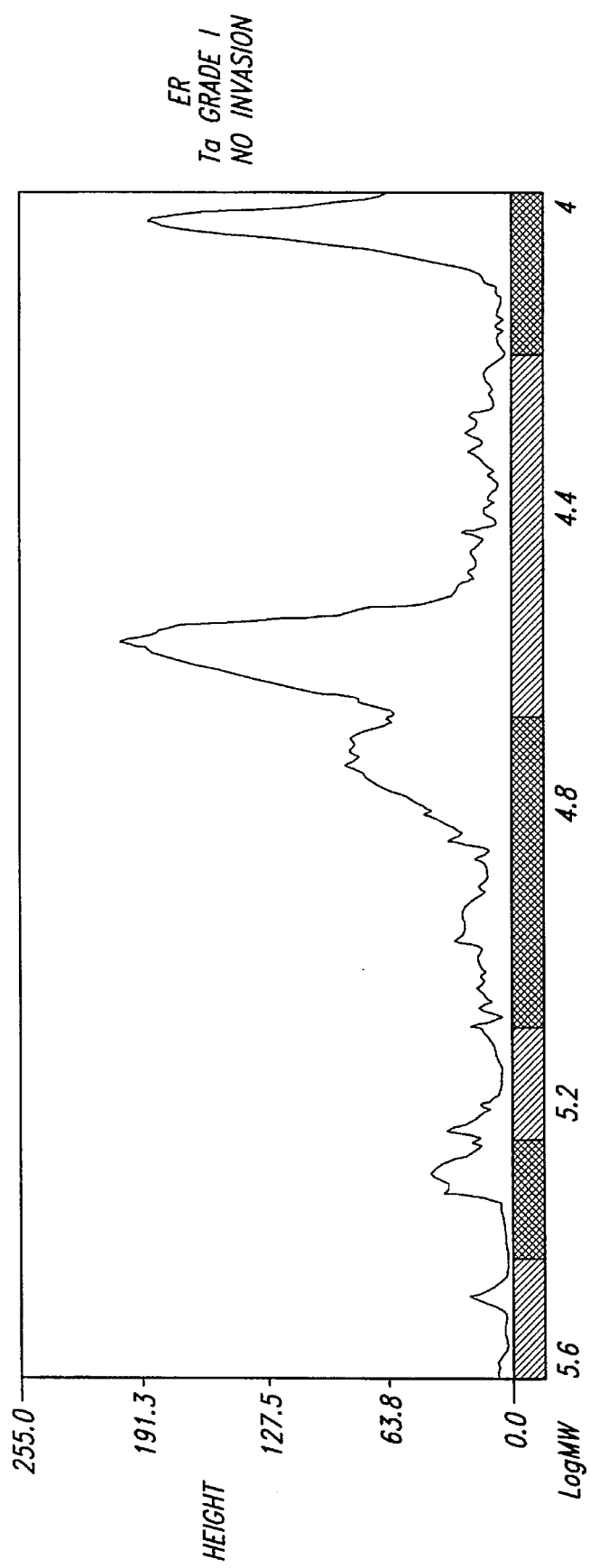
FIG. 4 graphically depicts SDS-PAGE profiles of fractionated urines of TCC patients of different stage and grade (Panels A–E).
Figure 4B:
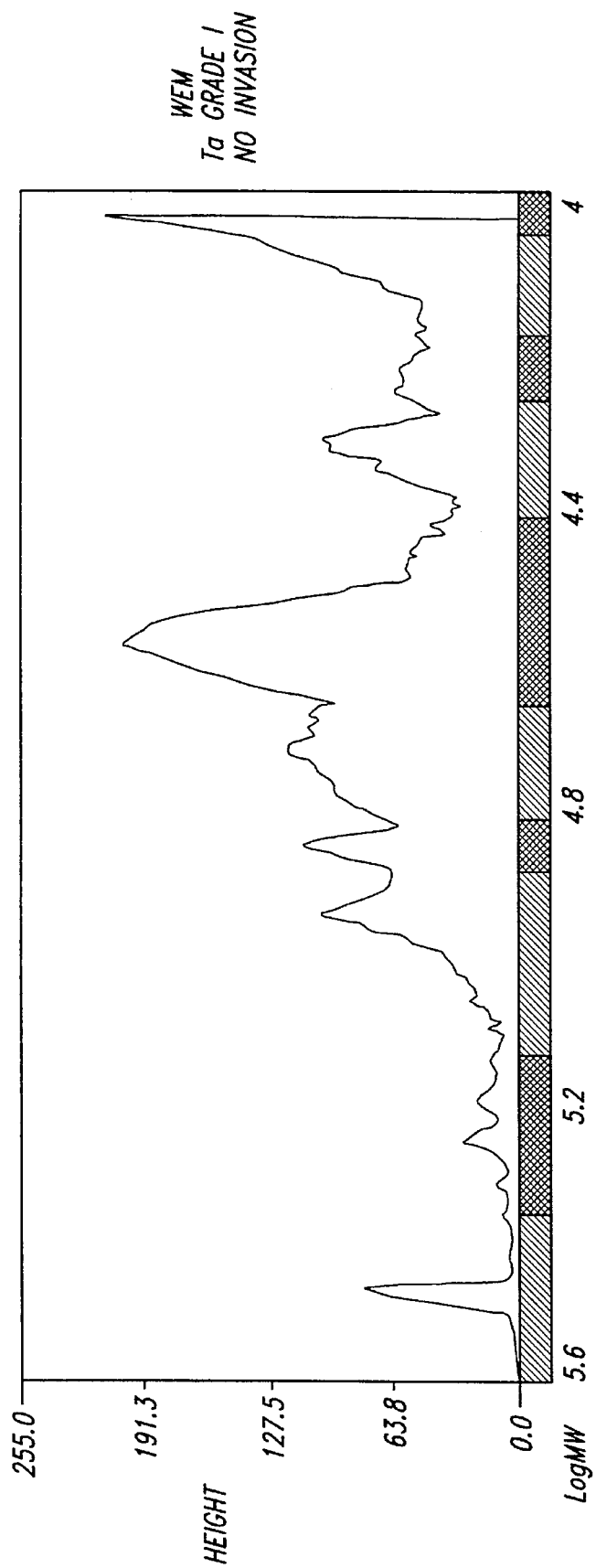
Figure 4C:
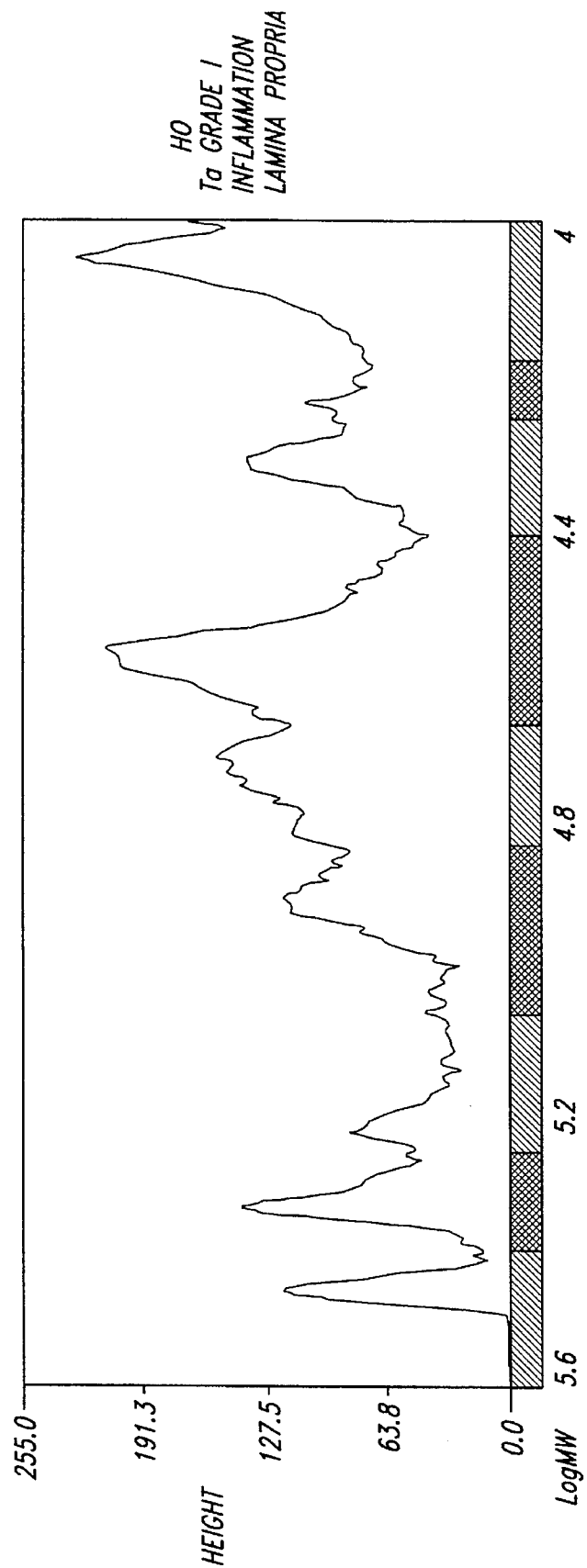
Figure 4D:
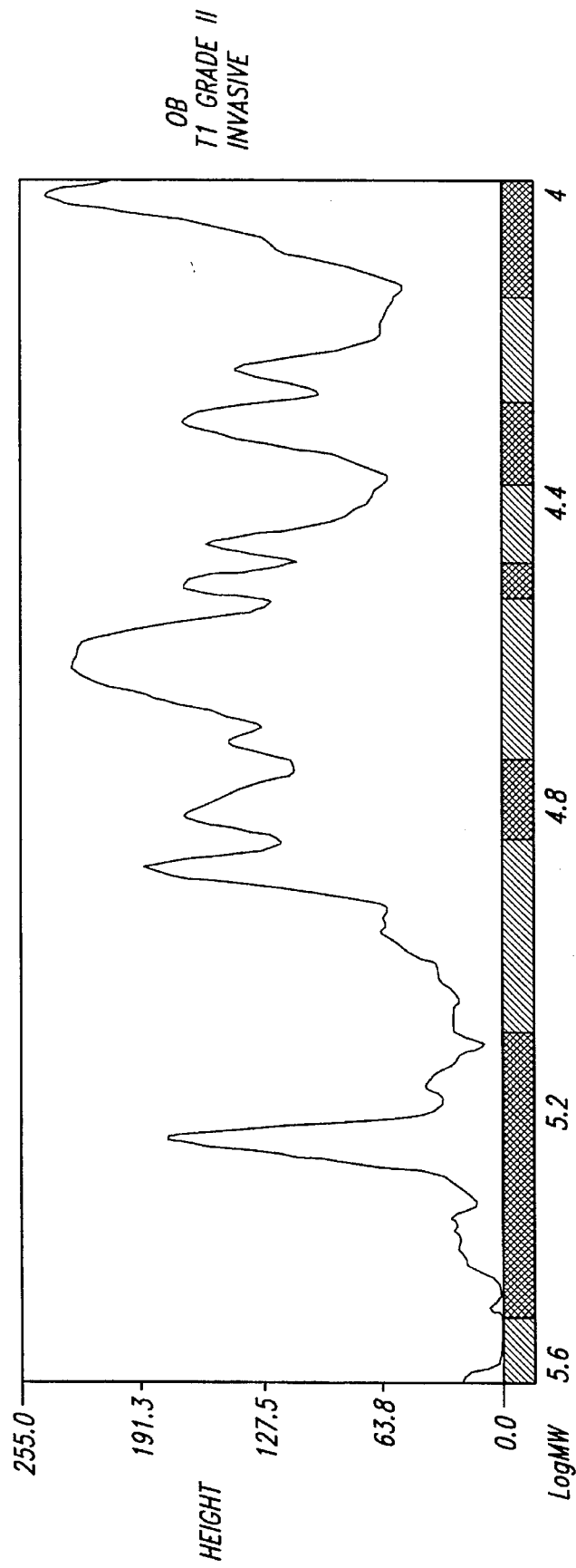
Figure 4E:
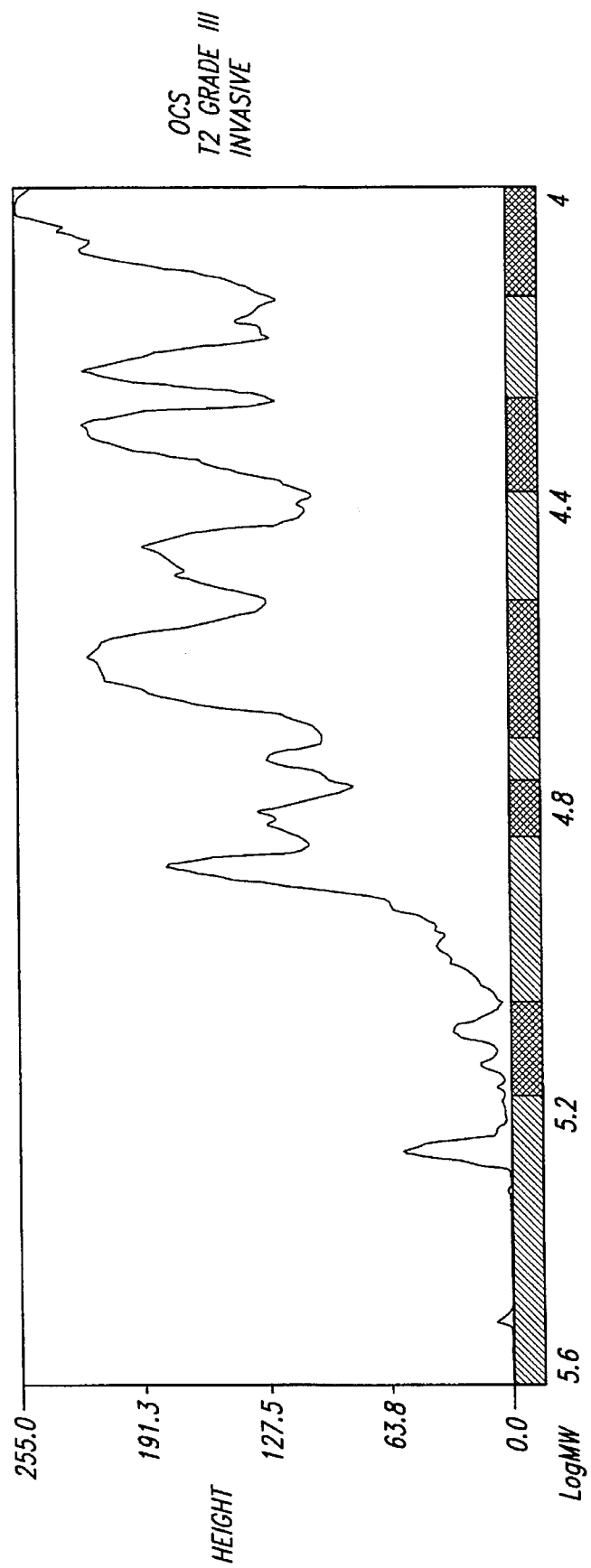

Twenty four hour urines (usually 500–3500 ml) upon receipt were initially tested using a urine dipstick (Chemstrip, Boehringer Mannheim) for pH, protein, microhematuria and for other urinary analytes, prior to testing in the BTA dipstick agglutination assay. After testing, the urines were treated with protease inhibitors [PMSF (5 mM), iodoacetamide (5 mM), benzamidine (2 mM) and EDTA (25 mM)], preserved with azide (0.1% w/v) and the pH adjusted to pH 7.4 with Tris buffer in order to stabilize against further proteolysis. Urines were then centrifuged and concentrated 50–100X on an Amicon PM30 membrane. The urine concentrate was then applied to an Agarose A1.5M column (2.5×50 cm column in earlier studies and 2.5×100 cm later) and eluted with 20 mM Tris buffered saline (0.13M) containing EDTA (25 mM) and benzamidine (2 mM). BTA dipstick agglutinating activity, if present, was measured using 35 μl of column fraction instead of urine as described in the assay procedure in Example 1. Activity was eluted at or near the void volume as seen in FIG. 2a for a TCC positive patient. In all cases the agglutinating activity was localized to the void volume. FIG. 2b shows a typical elution profile for a TCC negative patient which indicates little or no protein in the void volume fraction and no BTA activity.

Initial observations pointed to the fact that the positive agglutination reactivity in the void volume of the A1.5M agarose columns of fractionated bladder cancer urines also corresponded to fractions that reacted to several antibodies, although weakly, against native basement membrane proteins such as collagen IV and fibronectin and was indicative of high molecular weight complexes comprised of basal lamina components being present in these fractions.

These complexes were further purified. Active fractions from the A1.5M column were pooled, concentrated on an Amicon PM30 membrane, and applied to an Agarose A15M column (2.5×45 cm) and eluted in the same Tris buffer. Some protein elutes in the void volume but essentially all the agglutinating activity is in the included volume of the column, as shown in FIG. 3 for a number of TCC positive urines of different stage and grade. A direct correlation exists between the amount of BTA reactive material in urine and the stage/grade of a tumor, i.e., the more advanced the tumor the greater the quantity of BTA reactive material present in urine. This is discussed further in Example 3 below which relates activity in a larger number of gel filtration purified complexes to stage and grade of the tumor and to the molecular events occurring during the generation of the complexes.

EXAMPLE 3

RELATIONSHIP OF BTA DIPSTICK AGGLUTINATING ACTIVITY AND SDS PAGE PROFILES OF AGAROSE A15 FRACTIONS TO STAGE AND GRADE OF TUMOR

The BTA active fractions from A15 agarose gel filtration for the different urines were pooled and, if more than one column run was performed, active fractions of all columns for an individual patient were combined so as to represent the total isolated activity for a particular urine. Pools for each of the individual urines were then concentrated on a PM30 membrane and subjected to SDS-PAGE analysis in order to analyze the profile of protein bands present. Briefly, Agarose A15 purified complexes isolated from urines of patients with different stage and grade of TCC were subjected to SDS-PAGE using a 10%–12% polyacrylamide resolving gel in combination with a 5.6% stacking gel. Samples were diluted 3:1 in a 4X dissociation buffer (5% 2-mercaptoethanol in buffer mix of 1 ml of 1.5M Tris, pH 6.8, 4.8 ml of 10% SDS, 3.6 ml of Glycerol, 0.1 ml of 1% bromothymol blue and 2.4 ml of distilled water) and heated in a boiling water bath for 5 minutes. Samples were loaded onto gels at 2–10 μg/well along with wells containing molecular weight standards (205 kd–18.5 kd). Samples were run at 200V constant for ~45 minutes after which gels were removed and fixed in 40% methanol/10% glacial acetic acid prior to staining with either 0.1% Coomassie or BioRad silver stain. After destaining in the acetic acid methanol mix, bands were scanned on a densitometer. Molecular weights were then estimated based on known molecular weight standards included in the gel. Pre-stained molecular weight standards were obtained from BioRad (Richmond, Calif.). Depending on gel porosity, either high molecular weight standards (Myosin—205,000; β-galactosidase—116,500; Bovine serum albumin—80,000; and Ovalbumin—49,500) or low molecular weight standards (Phosphorylase B—106,000; Bovine serum albumin—80,000; Ovalbumin—49,500; Carbonic anhydrase—32,500; Soybean trypsin inhibitor—27,500; and Lysozyme—18,500) were used as per the manufacturer's recommendations. Pre-stained standards ran at higher molecular weights than their unstained counterparts.

Concentrates were also titered in the BTA dipstick assay by performing doubling dilutions of the pooled fractions in the A15M column butter and testing in the latex agglutination dipstick assay for positive reactivity. Protein concentrations were determined using a BCA protein assay (Bio-Rad). Specific activities for the different concentrates were then calculated (BTA positive assay titer/BCA protein concentration (mg/ml)) to determine if there was a correlation between the pattern of appearance of SDS bands with both BTA specific activity, (which is a measure of the amount of analyte) and stage or grade of tumor development. In addition, comparison of SDS-PAGE gels to those of normal urines, or non-TCC urines enabled the elimination of SDS-PAGE bands that were present in similar fractions from normal urine and therefore did not contribute to the BTA agglutination activity.

In A15 samples from normal urine pools, essentially no SDS-PAGE bands were visible with molecular weights in excess of 100 kd. In the case of TCC patients, however, patterns of high and low molecular weight bands were present that correlate with the progression and extent of disease. A summary of these patterns is given in Table 4 and densitometric scans of gels of A15 fractions of different stage and grade are shown in FIG. 4.

TABLE 4

Relationship of BTA Activity in Urine to Invasive Potential of Transitional Cell Carcinoma of the Bladder

| STATUS FOR TCC | TCC STAGE | ELECTROPHORETIC OBSERVATIONS | BTA ACTIVITY |
| --- | --- | --- | --- |
| Negative | | No high MW proteins > 100 kd | − |
| Low Grade Non-Invasive | Ta | 2 High MW proteins appear at 245 kd and 190 kd | ± |
| Low Grade Invasive | T1 | High MW proteins disappear and major bands appear at 165 kd and minor bands at 140 kd and 125 kd with lesser changes at lower MW | + |
| High Grade Invasive | T2–T3 | 165 kd, 140 kd and 125 kd begin to disapper with appearance of lower MW bands at 98, 82, 74, 55, 43, 35, 26 and 16 kd | ++ |

In early stage superficial tumors where invasive potential has not been established or not clearly evident as determined by cystoscopy, there is the appearance of high molecular weight peptides (≧190 kd). In particular, in some non-invasive tumors (Ta) and in cases of chronic epithelial inflammation there is the appearance of two bands at approximately 245 and 190 kd. Some of these tumors are weakly detectable in the BTA dipstick assay. Upon further progression and transition of the disease into an invasive phase, these bands gradually disappear and a major band of molecular weight approximately 165 kd appears along with lesser bands one at 140 kd and another at 125 kd with some minor changes at lower molecular weights. The presence of high BTA dipstick activity corresponds to the appearance of these proteins in particular the 165 kd peptide. As the tumor becomes more aggressive and invasive, these peptides are further degraded with the appearance of lower molecular weight species at approximately 98, 82, 74, 55, 43, 35, and 26 kd with indications of a lower MW band in the range of 16 kd, as evidenced in Western blots and higher percentage polyacrylamide gels. The 165 kd protein does not disappear completely when this transition occurs.

Figure 5A:
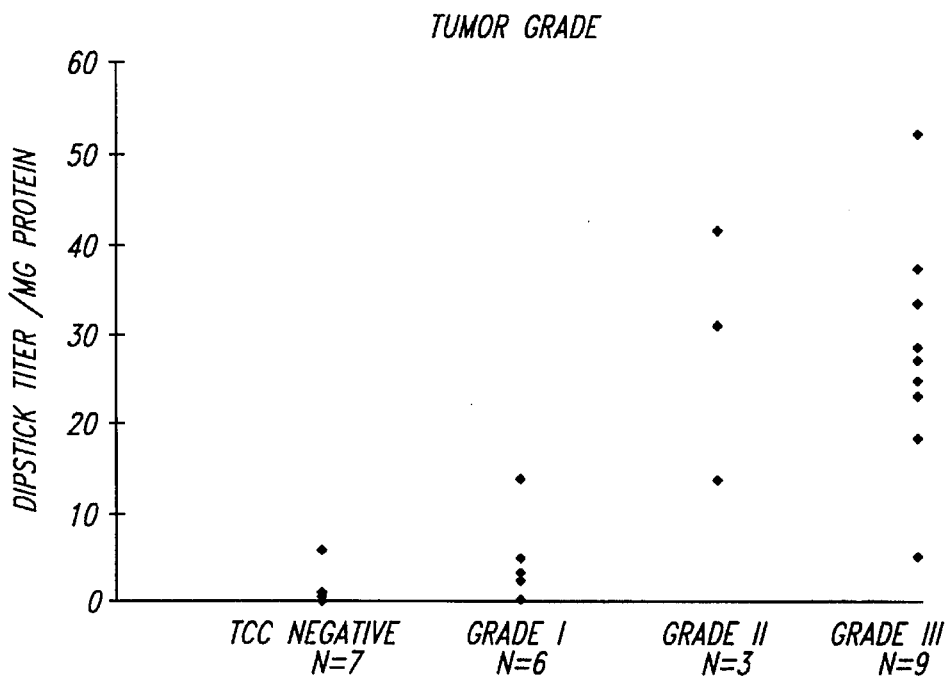
FIG. 5 graphically illustrates BTA dipstick activity versus tumor grade (Panel A) and tumor stage (Panel B) for A15 agarose purified fractions from 24 hour urines of bladder cancer patients and normals.
Figure 5B:
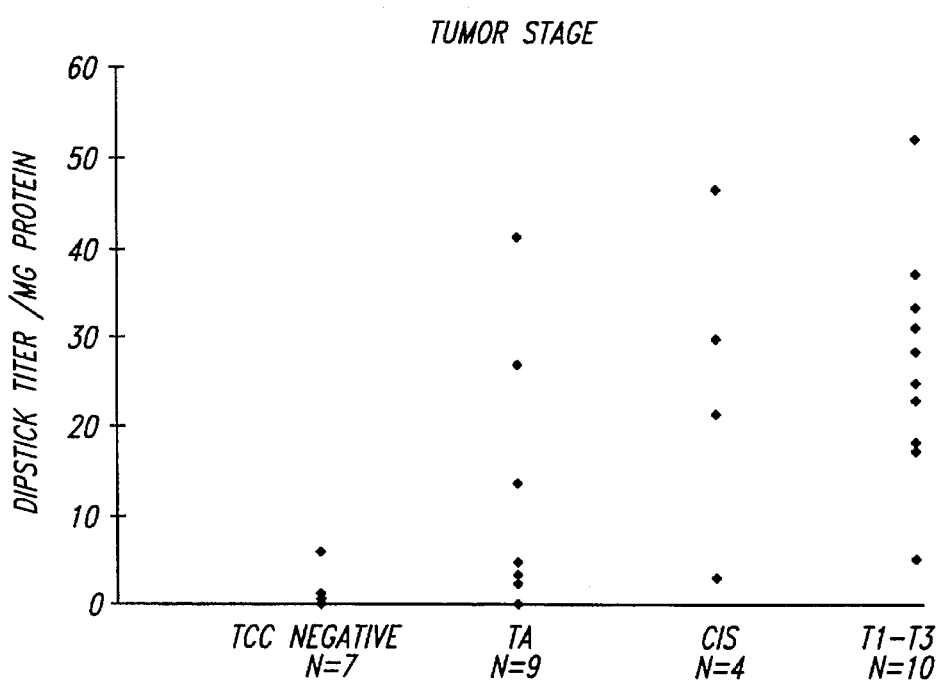

Analysis of the data of BTA specific activity versus the stage or grade of the tumor indicate a high degree of correlation with the stage and, in particular, the grade of the tumor and supports the utility of the BTA agglutination assays and hence the BTA analyte in the prognosis and monitoring of metasiatic transitional cell carcinoma of the bladder. FIGS. 5a and 5b show the relationship or stage and grade to activity in gel filtration purified complexes from several 24 hour urines and information on the urines and the mean specific activities versus stage and grade are given in Tables 5 and 6.

Initially, 1×20 cm Heparin agarose columns were equilibrated with 20 mM phosphate buffer, pH 7.4. Agarose A15 fractions were dialyzed overnight against this buffer and then applied to the heparin agarose column. 2-5 ml of sample was applied to the column and the column was

TABLE 5

BTA DIPSTICK SPECIFIC ACTIVITIES OF A15 AGAROSE PURIFIED COMPLEXES

| PATIENT ID | TCC STATUS | BTA TITER | PROTEIN µg/ml | SPECIFIC ACTIVITY |
|---|---|---|---|---|
| NEG POOL 1 | — | <1 | 3600 | 0 |
| NEG POOL 2 | — | <1 | 50 | 0 |
| NEG POOL 3 | — | <1 | <10 | 0 |
| WC | — | <1 | 600 | 0 |
| JCH | — | <1 | 175 | 0 |
| RES | BPH | <1 | 629 | 0 |
| LJB | CYSTITIS | 2 | 350 | 5.7 |
| JP | Ta GRADE I | 8 | 3600 | 2.22 |
| WEM(1) | Ta GRADE I | 4 | 890 | 4.49 |
| HO | Ta GRADE I | <1 | 810 | 0 |
| ER | Ta GRADE I | 1 | 220 | 4.55 |
| CDU | Ta GRADE I | 4 | 300 | 13.34 |
| TCH | Ta GRADE I | 128 | 42800 | 2.99 |
| HB | Ta GRADE II | 4 | 302 | 13.25 |
| CJS | Ta GRADE II | 8 | 195 | 41.03 |
| ELS | CIS | 16 | 544 | 29.41 |
| CES | CIS | 2 | 740 | 2.7 |
| WEW | CIS | 64 | 3060 | 20.92 |
| GWH | CIS | 256 | 5565 | 46 |
| OCS | T2 GRADE III | 64 | 2640 | 24.24 |
| MVA | T1 GRADE III | 32 | 1815 | 17.63 |
| OB | T1 GRADE II | 32 | 1050 | 30.48 |
| RN | T2 GRADE III | 8 | 155 | 51.61 |
| WAF | T2 GRADE III | 128 | 5700 | 22.46 |
| DM | T3 GRADE III | 512 | 15600 | 32.82 |
| AS | T3 GRADE III | 64 | 1750 | 36.57 |
| RB | T3 GRADE III | 16 | 573 | 27.92 |
| DEW | T3 GRADE I(?) | 64 | 3800 | 16.84 |
| HS | T3 GRADE III | 8 | 1695 | 4.72 |
| POM | Ta GRADE III | 64 | 2410 | 26.56 |

TABLE 6

RELATIONSHIP OF BTA DIPSTICK SPECIFIC ACTIVITY TO STAGE AND GRADE OF TCC MEAN SPECIFIC ACTIVITY (Titer/mg) VS STAGE AND GRADE

| NORMALS | (n = 7) | 0.8 |
|---|---|---|
| GRADE I | (n = 6) | 4.6 |
| GRADE II | (n = 3) | 28.3 |
| GRADE III | (n = 9) | 27.2 |
| Ta | (n = 9) | 12.1 |
| CIS | (n = 4) | 24.8 |
| T1 | (n = 2) | 24.1 |
| T2 | (n = 3) | 32.8 |
| T3 | (n = 5) | 23.8 |

EXAMPLE 4

HEPARIN AGAROSE FRACTIONATION AND SDS PROFILES OF COMPLEXES

Figure 6:
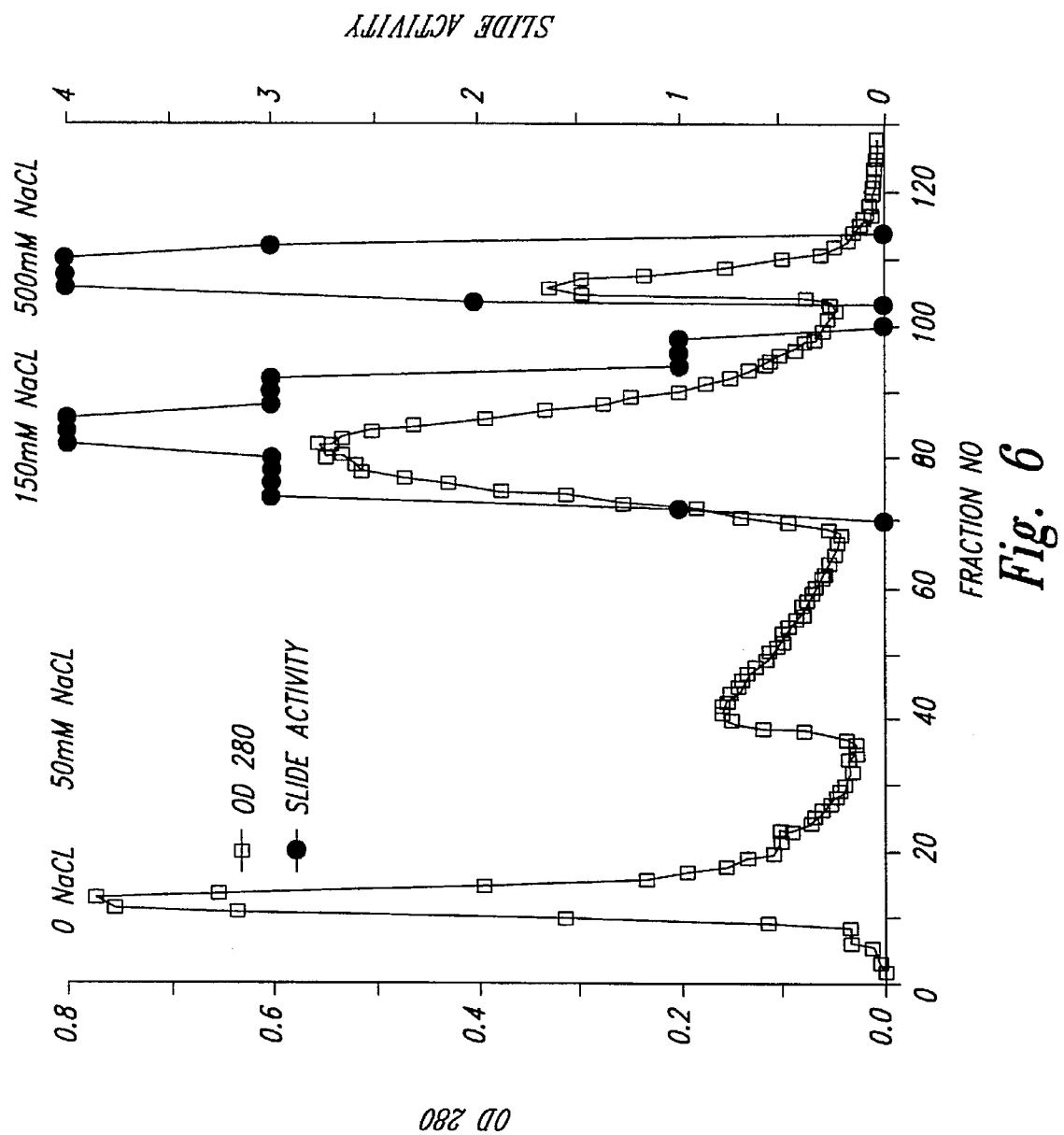
FIG. 6 graphically depicts fractionation of gel filtration purified BTA complexes on heparin agarose using a phosphate buffer system.

To further pinpoint the peptides contributing to the BTA activity, positive samples after agarose A15M were further fractionated on Heparin agarose which is known to bind fibronectin and laminin and has been shown to bind the BTA reactive complexes with high affinity. The active fractions were again analyzed by SDS gel electrophoresis. From these studies, protein bands were clearly identified as contributing to the core agglutinating activity.

washed with equilibration buffer to elute non binding material that was devoid of BTA activity. The column was now eluted with a 0-500 mM stepwise gradient of NaCl in equilibration buffer (0, 50, 150 and 500 mM). The BTA activity eluted in 100-150 mM salt. A second peak of activity was also seen when a 500 mM wash was used. A typical elution profile from Heparin agarose when using a phosphate buffer system is shown in FIG. 6. This shows the fractionation of a high stage and grade (T3 Grade III) tumor.

Figure 7:
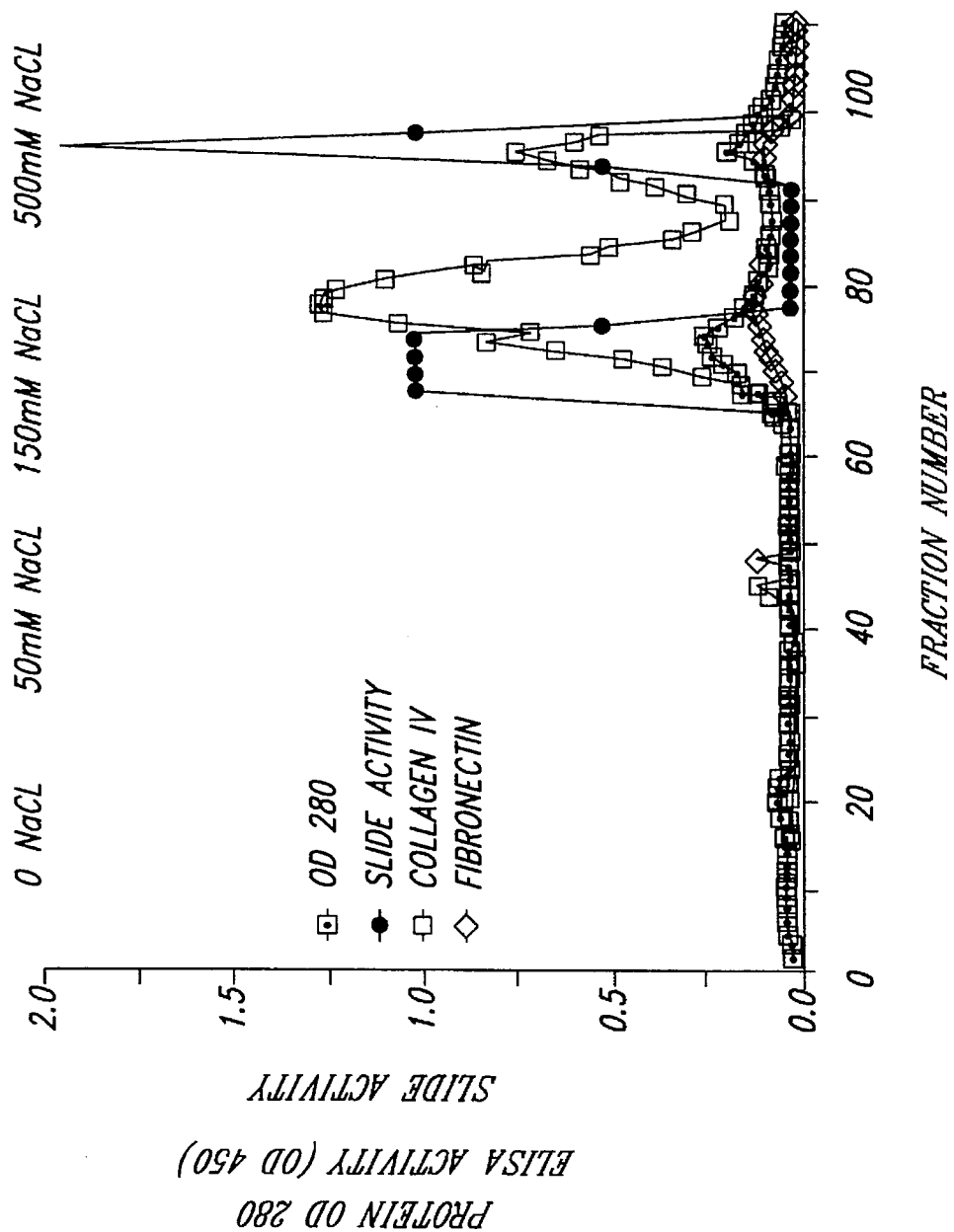
FIG. 7 graphically illustrates fractionation of heparin agarose purified complexes on DEAE-Biogel A.

Cytokeratin (a previously described potential marker for bladder cancer) was detectable in the flow through of the column using a cytokeratin antibody clone 8.13 and was not detectable in the BTA reactive fractions. Both of the agglutinating fractions were then concentrated on an Amicon PM10 membrane and re-dialyzed against 20 mM sodium phosphate buffer, pH 7.4, and applied separately to a 1×20 cm DEAE-Biogel A column (BioRad, Richmond, Calif.). Fractions were again eluted with 20 mM phosphate buffer, pH 7.4, containing 0, 50, 150 and 500 mM sodium chloride. Fractions were tested for BTA activity and in an ELISA assay with anti-type IV collagen and anti-fibronectin antibodies. The majority of the agglutinating activity in the 150 mM fraction from heparin agarose also appeared in the 150 mM fraction from DEAE-Biogel A with a small portion of the activity in the 500 mM fraction. The opposite was seen (FIG. 7) with the 500 mM Heparin agarose fraction after separation on DEAE-Biogel A. Both the 150 and 500 mM DEAE fractions showed reactivity in the slide agglutinating assay and were reactive with antibodies to Type IV collagen and fibronectin although weakly thus indicating the two proteins purifying as a complex.

Figure 8:
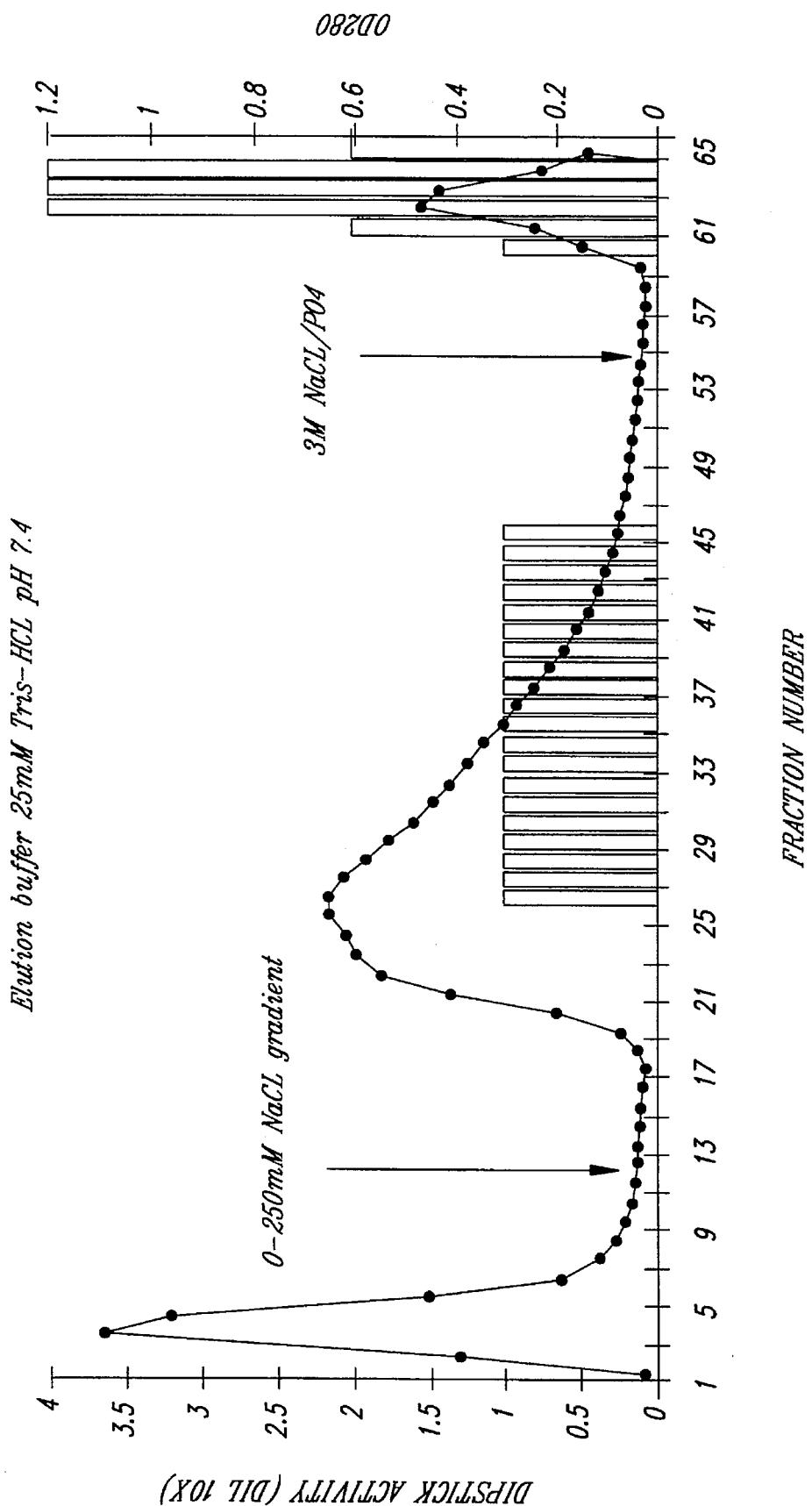
FIG. 8 graphically depicts fractionation of gel filtration purified BTA complexes on heparin agarose using a Tris-buffer system.

In later studies, 5–10 ml heparin agarose columns were equilibrated with 25 mM Tris, pH 7.4. Agarose A15 fractions were dialyzed overnight against the equilibration buffer and applied to the heparin agarose column. 2–5 mls of sample was applied to the column and the column was washed with equilibration buffer to elute non-specific material that was devoid of BTA activity. The column was now eluted with a 0–500 mM linear gradient of NaCl in equilibration buffer. The BTA activity eluted in 100–150 mM salt. A second peak of activity was also seen when a 500 mM NaCl/25 mM phosphate buffer, pH 7.4, elution buffer was used. Typical elution profiles from heparin agarose when using a Tris buffer system are shown in FIG. 8. These represent fractionations of two urines representative of high and low grade TCC and one negative urine. Application of a salt gradient results in activity appearing as a trailing shoulder to a major protein peak at a salt concentration of 100–150 mM. This shoulder of activity in the 100–150 mM fraction was absent in BTA negative urines and in the case of a Ta urine patient, HB, which had little or no BTA activity. Earlier studies showed that the peak eluting in the flow-through which was devoid of BTA activity, was enriched for cytokeratins another marker which has been utilized as a bladder cancer marker. The complexes derived from bladder cancer patients, however, react poorly with antibodies to collagen IV and fibronectin as outlined in earlier studies on heparin agarose (see above).

Figure 9:
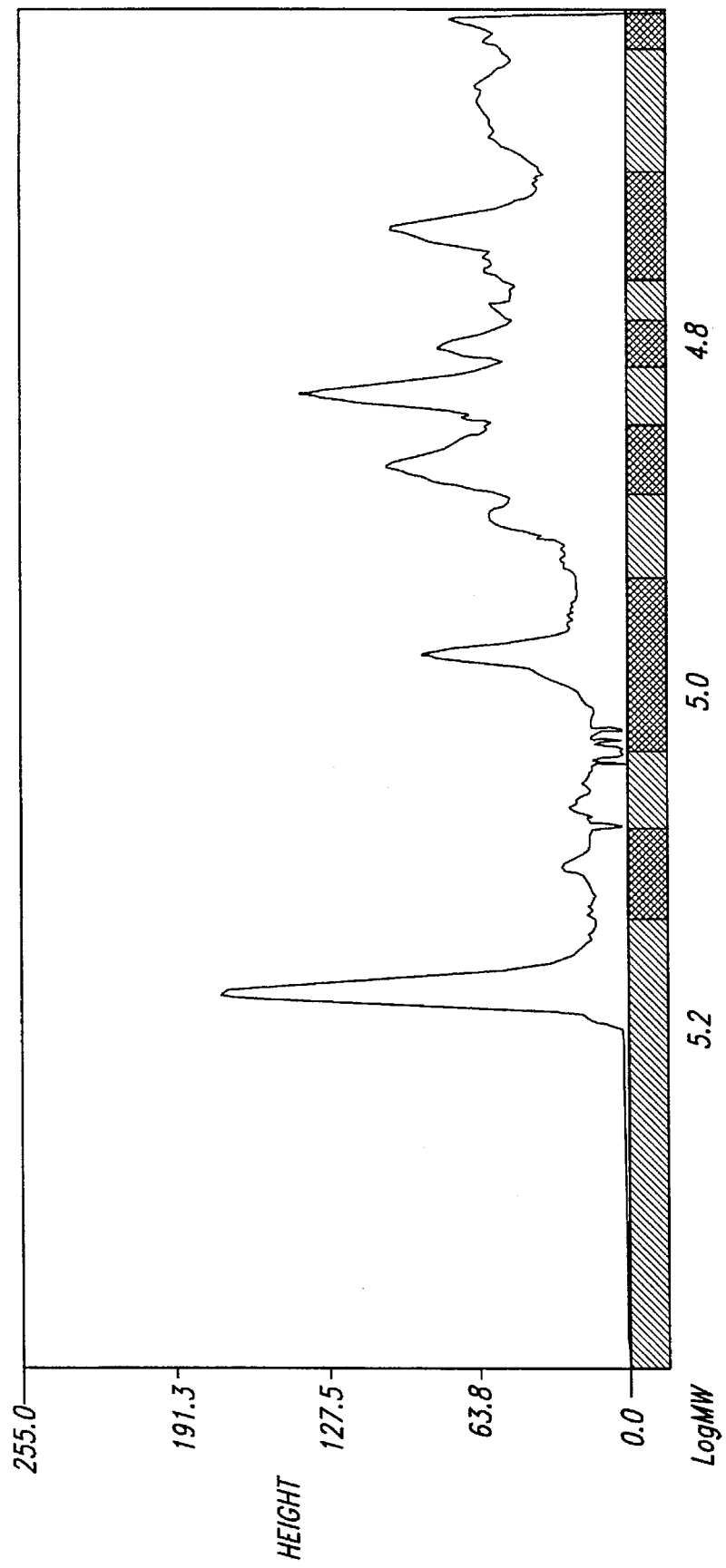
FIG. 9 graphically illustrates SDS-PAGE of heparin agarose purified BTA complex from a TCC patient.

An example of the SDS polyacrylamide analysis of heparin agarose fractions with BTA activity from Tris buffer eluted heparin agarose columns is shown in FIG. 9. The SDS bands seen were absent from a normal urine pool and appear to represent the core components of the complexes. The molecular weights again show the same group of polypeptides described in Example 3.

EXAMPLE 5

DEVELOPMENT AND CHARACTERIZATION OF ANTIBODY (1B4) TO COMPLEX

BALB/c mice were immunized with 100 µl of a 1:1 mixture of A15 agarose purified material from a TCC patient with T2 grade III tumor with Freund's complete adjuvant. Two secondary immunizations at monthly intervals with the 165 kd material isolated by SDS/PAGE electroelution from the same patient were peribrined in 1:1 mixture in Freund's incomplete adjuvant. A final boost of electroeluted material in Freund's incomplete adjuvant was administered after a further 3 weeks and one week prior to sacrificing the mice.

Spleen cells were prepared in serum-free RPMI 1640 medium and mixed with P3/NS-1/1-Ag4-1 cell line in a Spleen cell/NS-1 cell ratio of 5:1 in a total volume of 25 ml. This cell mixture was centrifuged at 1200 g for 10 minutes at room temperature. Supernatant was removed and the cells resuspended in serum free medium and re-centrifuged. Cells were washed three times in this manner. After removing the final supernatant, the cell pellet was gently resuspended in the residual medium by gently tapping the tube and warming in 37° C. water bath for 1 minute. The fusion procedure was initiated by the addition of 300 µl of 45% (w/v) polyethylene glycol (Boehringer Mannheim) at 37° C. over a period of 45 seconds while agitating gently. Cells were gradually diluted by the addition of 15 ml of serum-free medium over a period of 90 seconds. Cells were centrifuged gently and the supernatant removed. Cells were then gently re-suspended in 70 ml of HAT medium (no vortexing) and dispensed into 96 well plates at 100 µl/well. Plates were then incubated at 37° C. for 7–10 days after which supernatants from hybridoma containing wells were tested by ELISA against a panel of electroeluted antigens of differing molecular weights from the original A15 agarose isolated immunogen and commercially available basement membrane proteins. Wells were selected on the basis of their reactivity with A15 antigens and non-reactivity with intact basement membrane proteins.

Selected wells were grown up in RPMI 1640 medium containing 20% Fetal bovine serum, single cloned and screened for activity against the basement membrane proteins and high molecular weight complexes from a panel of A15 antigens from several TCC positive and negative patients. Cell lines were single cloned a total of 3 times and in each case screened as above.

For screening purposes, 96 well plates were coated with the basement membrane proteins human fibronectin, laminin and collagen IV in addition to fibrinogen and A15 purified complexes from TCC positive and negative urines as well as electroeluted material from TCC positive urines. Coating in each case was performed at 4 µg/ml in carbonate/bicarbonate buffer, pH 9.6, using 100 µl/well of antigen and, after overnight incubation of the plates, were blocked in PBS containing 1% bovine serum albumin. Clones were selected for lack of reactivity to basement membrane proteins, fibrinogen and A15 purified urines of TCC negative patients, but for positive reactivity with A15 material from TCC positive urines. While screening supernatants, 50 µl of hybridoma supernatant was added to wells containing the appropriate antigen and incubating for 1 hour at room temperature. Wells were then aspirated and washed three times in PBS-Tween buffer after which goat anti-mouse IgG horse radish peroxidase conjugate was added to the wells and the plates incubated for a further 1 hour at room temperature. Plates were then washed 3 times in PBS-Tween and the presence of bound horse radish peroxidase conjugate detected using TMB substrate. Reactions were stopped with the addition of 100 µl of 1N $H_2SO_4$. Plates were finally read at 450 nm in an ELISA reader. Control wells with antibodies to basement membrane proteins were used when appropriate. Antibody 1B4 and similar clones 3D6, 1A3 and 8H2 all were reactive with the electroeluted 165 kd component of the complex, but were non-reactive with human Collagen IV, Laminin, fibronectin and fibrinogen as shown in Table 7.

TABLE 7

ELISA REACTIVITIES OF BTA CLONES WITH BASAL LAMINA AND RELATED PROTEINS

| SOLID PHASE ANTIGEN | ELSIA REACTIVITY (OD 450) | | | |
| --- | --- | --- | --- | --- |
|  | 1B4 | 3D6 | 8H2 | 1A3 |
| Collagen IV | 0.01 | 0.017 | 0.005 | 0.004 |
| Fibronectin | 0.01 | 0.005 | 0.008 | 0.013 |
| Laminin | 0.056 | 0.027 | 0.026 | 0.061 |
| Fibrinogen | 0.160 | 0.101 | 0.07 | 0.155 |
| Electroeluted 165 kd | >3.0 | >3.0 | >3.0 | >3.0 |

Reactivity of the antibodies with purified complexes from urines and with the urines themselves is described in Example 8.

The 1B4 antibody was also shown to inhibit both dipstick and slide agglutination activity directly in urine samples.

Figure 10:
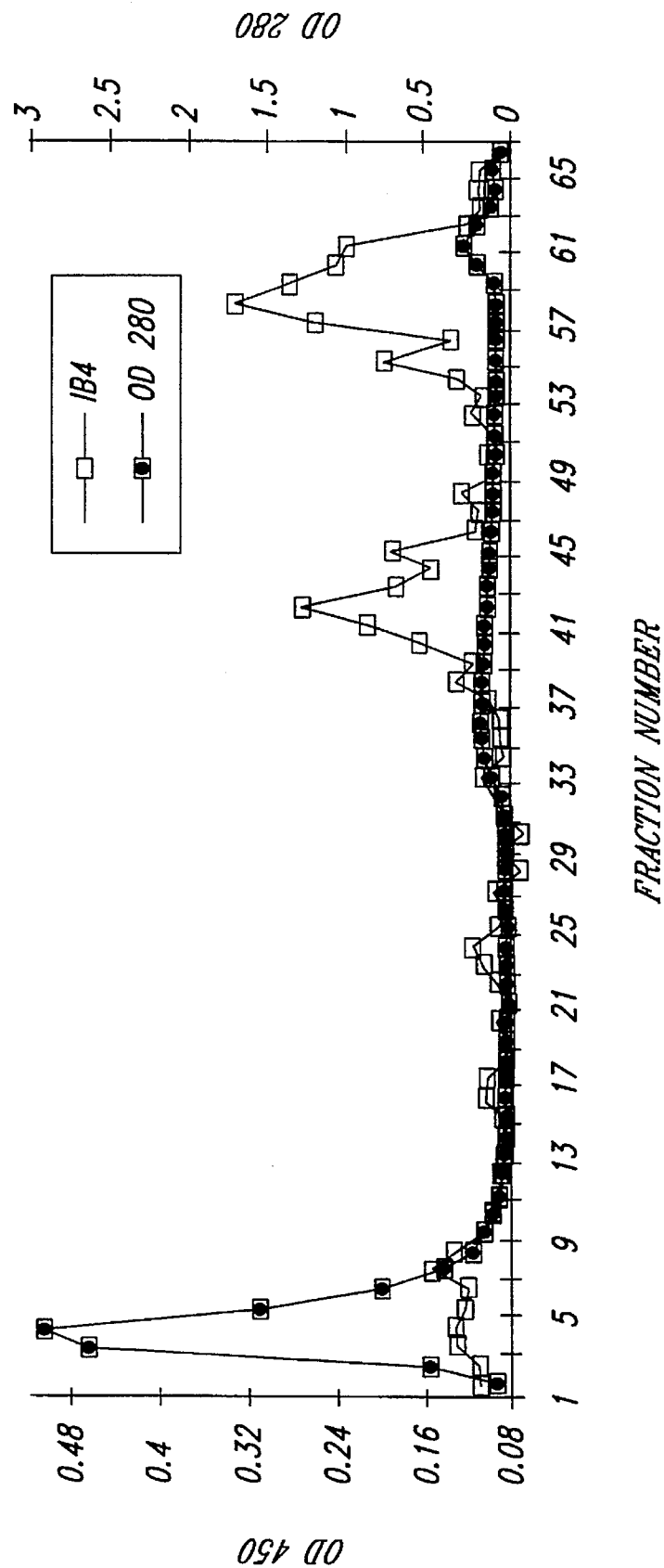
FIG. 10 graphically depicts 1B4 immunoreactivity with fractions from heparin agarose purification of complexes directly from urine of Ta Grade 1 patients.

1B4 antibody was also tested for reactivity against fractions from a heparin agarose fractionation of the urine of a patient with TCC to determine if reactivity is located in the BTA reactive fractions. The data (FIG. 10) shows that 1B4 reactivity is located in the same salt fractions as seen in Example 4 further demonstrating the reactivity of the 1B4 antibody with the complexes.

The 1B4 antibody was isotyped using Mabcheck (Sterogene, Calif., U.S.A.) and shown to be of the IgG1(K) type. The cell line which produces antibody 1B4 was deposited with American Type Culture Collection and designated as ATCC No. 11389.

The procedures described above for developing antibodies to the complexes is also applicable to the development of antibodies to the individual components. These proteins can be isolated by electroelution from the complexes and used as immunogens, followed by screening for lack of reactivity to basal lamina proteins but with activity to urines, or isolated fractions of urines, from bladder cancer patients.

EXAMPLE 6

ELISA REACTIVITY OF 1B4 WITH A15 PURIFIED FRACTIONS OF PATIENTS WITH DIFFERENT STAGE AND GRADE OF CANCER

A. Heparin Capture ELISA

Based on the fact that the complexes have a high affinity for heparin, assays were performed that utilized heparin as a solid phase to capture the complexes from urine samples or from gel filtration purified complexes.

Ninety-six well ELISA plates were coated overnight with 100 µl of Heparin (4 µg/ml) in 50 mM carbonate/bicarbonate buffer, pH 9.6, and aspirated dry. Gel filtration purified (Agarose A15) samples from urines of patients with different stage and grade of TCC were diluted to 4 µg/ml in 25 mM Tris-HCl, pH 7.8. One hundred microliters of this dilution was added to the heparin coated plates and incubated at 37° C. for two hours. Plates were then aspirated and 100 µl 1B4 antibody (1–2 µg/ml) was added to each of the wells and plates incubated for 2 hours at room temperature. Plates were then washed 3 times in phosphate buffered saline containing 0.1% Tween 20 prior to the addition of 100 µl of a 1/2000 dilution of goat anti-mouse IgG-horse radish peroxidase (HRP) conjugate in phosphate buffered saline containing 0.1% Tween 20 and 0.1% bovine serum albumin. Plates were then incubated for 1 hour at room temperature then washed 3 times in PBS-Tween. Detection of HRP-labeled immunocomplexes in the wells was achieved by adding 100 µl of TMB substrate to the well, incubating for 30 minutes at room temperature, then stopping the reaction by adding 100 µl of 1N $H_2SO_4$. Wells were read at 450 nm in an ELISA reader.

Figure 11:
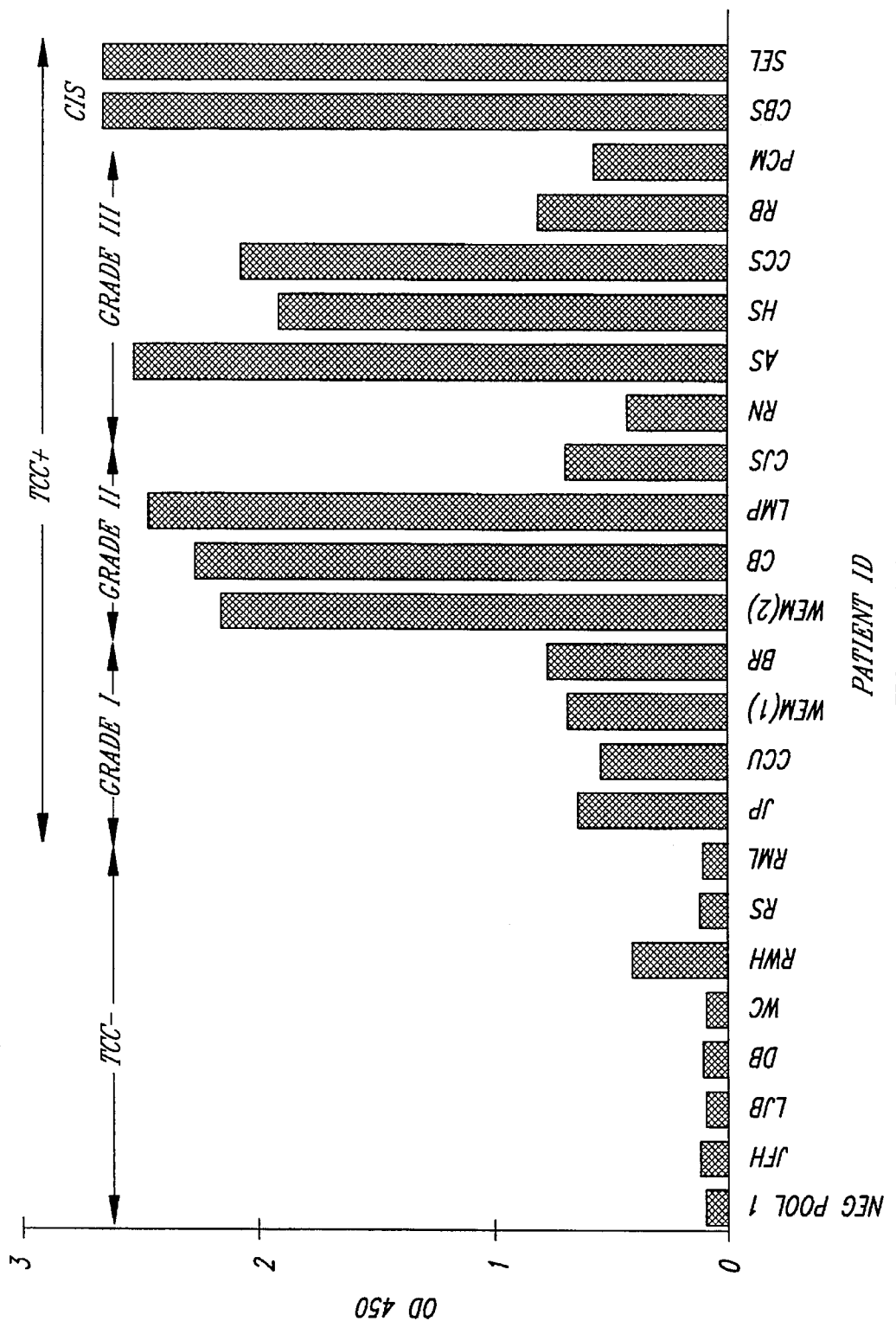
FIG. 11 graphically illustrates a heparin capture ELISA system using 1B4 antibody and A15 purified complexes from TCC patients and normals. A total of 8 TCC negative and 16 TCC positive gel filtration isolated complexes were studied.

FIG. 11 shows the reactivity of 24 different A15 purified complexes (16 TCC positives and 8 TCC negatives). Of the 16 positives, all were detected by the heparin capture EIA. Of the negatives, only one showed some reactivity which was shown to be a Stage D prostate cancer which had metastasized beyond the prostate. FIG. 11 also shows that the overall ELISA reactivity appears to increase as the grade increases as might be expected from the data in previous examples. The samples from the CIS patients, which typically have high grade tumors, were also highly reactive.

B. Non-Heparin ELISA

A15 purified fractions were diluted to 4 µg/ml with 50 mM carbonate/bicarbonate coating buffer, pH 9.6, and coated onto the wells of a 96 well microtiter plate and incubated ovenight at 4° C. Plates were then aspirated and 100 µl of blocking buffer (phosphate buffered saline, pH 7.4, containing 2% BSA) was added and the plates incubated for 90 minutes. The wells were then aspirated and 100 µl of 1B4 antibody (1–2 µg/ml) in phosphate buffered saline pH 7.4 containing 0.1% (v/v) Tween 20 and 0.1% (w/v) bovine serum albumin was added to each of the wells and the plates incubated for a further 2 hours at room temperature. After washing the plates 3 times in phosphate buffered saline containing 0.1% Tween 100 µl of goat anti-mouse IgG-horse radish peroxidase conjugate (1/2000 dilution) in phosphate buffered saline, pH 7.4, containing 0.1% bovine serum albumin and 0.1% Tween 20 was added to each of the wells and the plate incubated at room temperature for 1 hour. Plates were again washed three times as before prior to adding TMB substrate to each of the wells. Color was allowed to develop for 30 minutes at which time the reaction was stopped by the addition of 100 µl of 1N $H_2SO_4$ and read on an ELISA reader at 450 nm.

Figure 12:
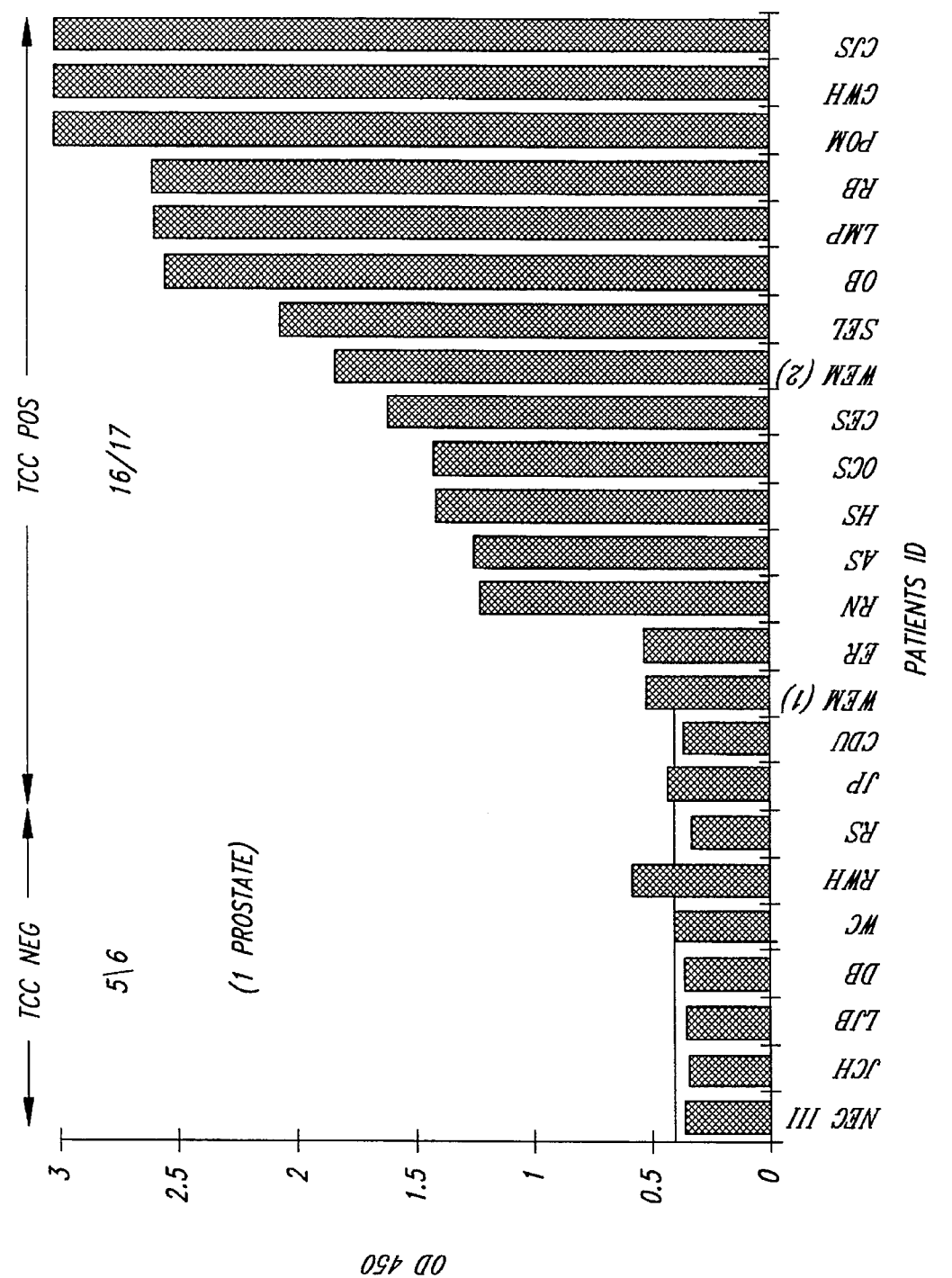
FIG. 12 graphically depicts a direct ELISA system using 1B4 antibody and A15 purified complexes as solid phase antigen.

FIG. 12 shows the reactivity of several TCC positive and negative urines with the 1B4 antibody where A15 material is isolated from these urines and is coated directly onto the wells of a polystyrene plate as described in the above procedure. Again, differentiation of TCC positive and negative urines was possible, although the signal was diminished as compared to the heparin capture ELISA when urines are used directly.

EXAMPLE 7

ELISA REACTIVITY OF 1B4 RELATED SUBCLONES WITH BASEMENT MEMBRANE COMPLEXES

Figure 13:
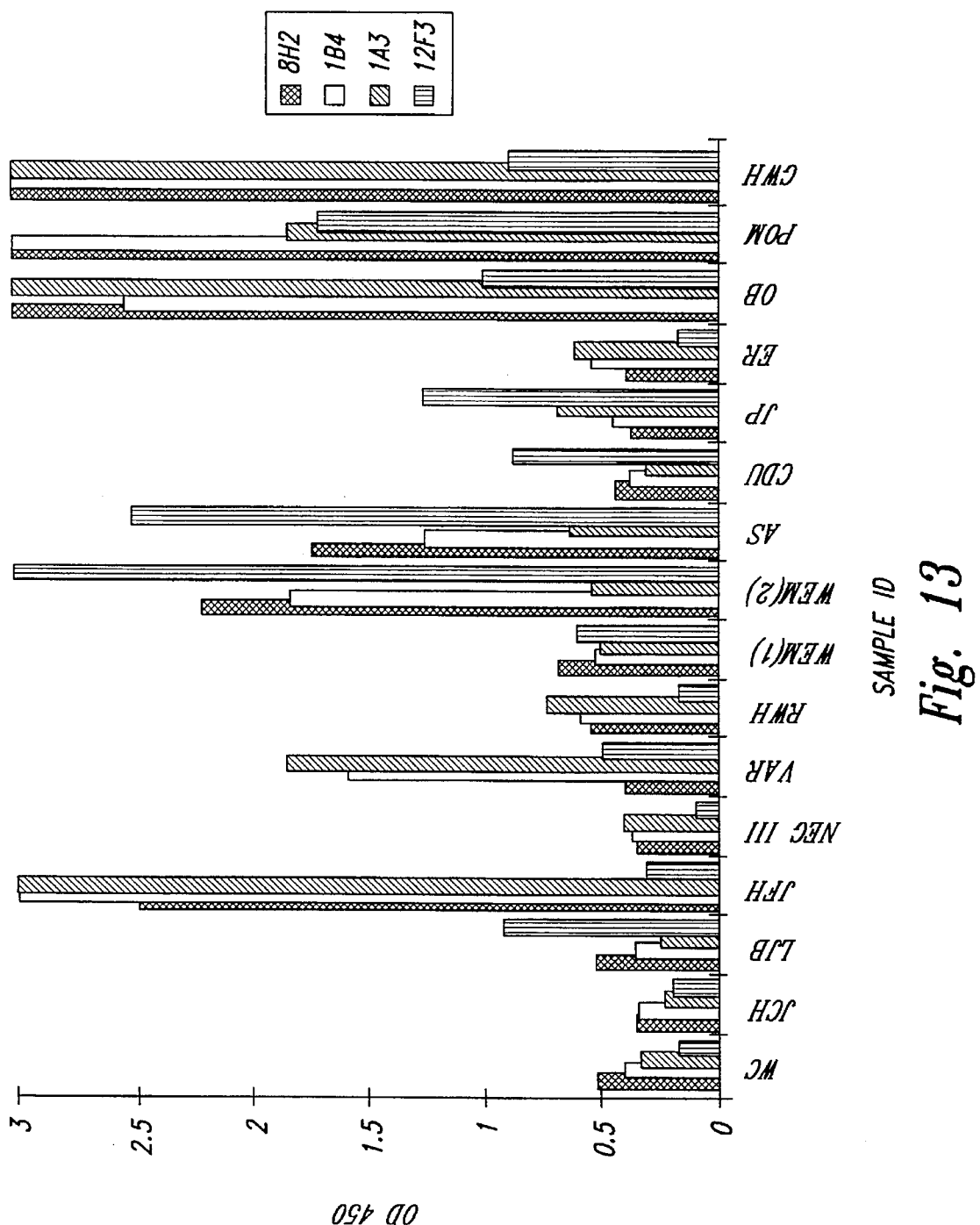
FIG. 13 graphically illustrates the reactivity of 1B4 related clones with A15 purified complexes of TCC positive and negative patients.

From the same fusion as the 1B4 clone was derived, several other clones or sister clones were developed and tested in ELISA assays as described above, against A15 purified material and also against urines directly. Of particular note are the sister clones 1A3 and 3D6 isolated from the same well as 1B4. Another clone 8H2 was derived from the same fusion as 1B4. Clone 12F3 was isolated from another mouse immunized and fused in the similar way to that from which the 1B4 clone was derived. The clones 12F3 and 8H2 while having similar ELISA reactivity to 1B4 do have differences in their reactivity in Western Blot analyses that indicate that they bind to different epitopes and therefore useful in sandwich ELISA assays. FIG. 13 shows the ELISA activities of these clones as compared to 1B4. Information on the differences in Western blot analysis is given in Example 10 below.

EXAMPLE 8

ELISA REACTIVITY OF 1B4 WITH URINES FROM BLADDER CANCER PATIENTS

Heparin Capture ELISA

Ninety-six well ELISA plates were coated overnight with 100 µl of heparin (4 µg/ml) in 50 mM carbonate/bicarbonate buffer, pH 9.6, and were aspirated dry. Urines were buffered by adding 1 part of 500 mM Tris-HCl buffer, pH 7.4, to 4 parts of urine for a final concentration of 100 mM Tris buffer. One hundred microliters of this dilution was added to a heparin coated plate. Plates were incubated at 37° C. for 2 hours. Plates were then aspirated and 100 µl 1B4 antibody (1–2 µg/ml) in phosphate buffered saline containing 0.1% Tween 20 and 0.1% bovine serum albumin was added to each of the wells and plates incubated for 2 hours at room temperature. Plates were then washed 3 times in phosphate buffered saline containing 0.1% Tween 20 prior to the addition of 100 μl of a 1/2000 dilution of goat anti-mouse IgG-horse radish peroxidase (HRP) conjugate in phosphate buffered saline containing 0.1% Tween 20 and 0.1% bovine serum albumin. Plates were then incubated for 1 hour at room temperature then washed 3 times in PBS Tween. Detection of HRP-labeled immunocomplexes in the wells was achieved by adding 100 μl of TMB substrate to the well incubating for 30 minutes at room temperature then stopping the reaction by adding 100 μl of 1N $H_2SO_4$. Wells were read at 450 nm in an ELISA reader.

Figure 14:
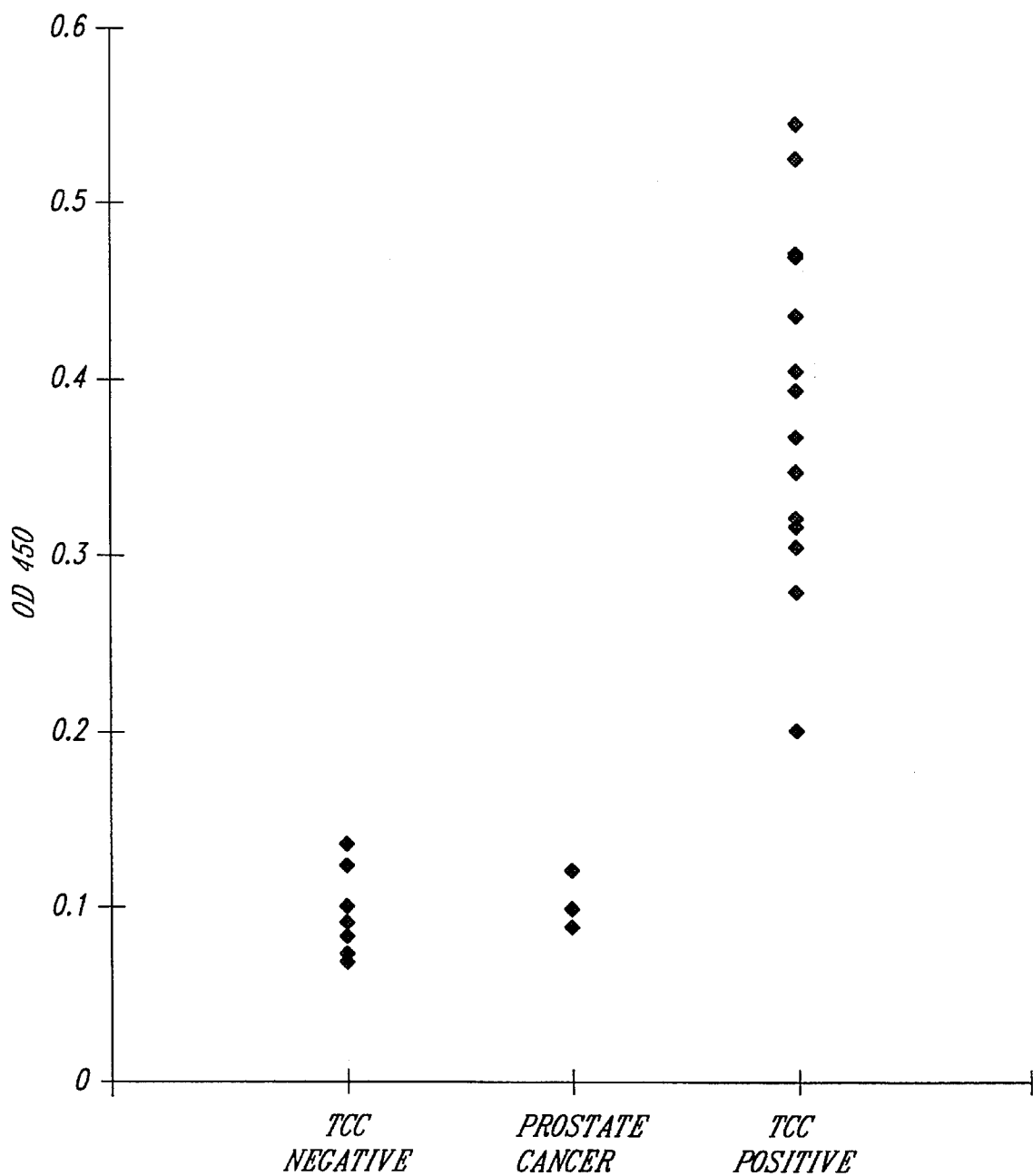
FIG. 14 graphically depicts the distribution of 1B4 ELISA reactivities with urines from urological patients. A total of 26 patients were studied, with 15 confirmed TCC positives and 11 TCC negatives of which 3 were prostate cancers of stage B1, C3 and C1.

FIG. 14 shows the ELISA reactivity of positive and negative urines when tested in this assay format and supports the use of the 1B4 antibody in the detection of TCC positive urines.

EXAMPLE 9

1A3 DIPSTICK REACTIVITY WITH URINES FROM BLADDER CANCER PATIENTS

Clone 1A3 is a sister clone to 1B4 with identical properties. This antibody was purified on Protein A sepharose and bound passively to latex particles as described below.

150 ml of de-ionized water was added to 50 ml of 48% Lytron 5450 latex suspension (Morton Thiokol International) and centrifuged for 2 hours at 8000 rpm. This wash step was repeated a second time. The latex was then resuspended to a 10% (w/v) in 10 mM phosphate buffered saline, pH 7.4. Sixty five microliters of purified 1A3 monoclonal antibody (300 μg/ml) in 10 mM phosphate buffered saline was then added first to 10 ml of 10% Lytron 5450 particles followed by 100 mg of bovine serum albumin as a blocking agent. The latex suspension was mixed for 6 hours at room temperature on a rotator. Brilliant blue R ( Sigma Chemical Co., 5 mg) was now added to the mixture and the suspension mixed for a further 1 hour. This constituted the stock latex reagent.

Following incubation and blocking with BSA, 1 ml of the stock latex was mixed with 9 ml of 0.1M glycine buffer, pH 8.2, containing 0.075% Bovine serum albumin and 1 ml/liter of yellow food coloring (Crescent). This constituted the working latex reagent.

To test the reactivity of the antibody coated latex, 20 μl of patient urine was mixed with 80 μl of working latex and mixed in a well comparable to that used for the BTA assay in Example 1. After letting the reagent sit for 20 seconds at room temperature a controlled pore size glass fiber dipstick was added to the reaction mix. The dipsticks were interpreted as positive or negative in the same manner as the dipstick assays described in Example 1. Urine samples were also tested in the buffered urine BTA dipstick assay as described in Example 1. Samples were chosen that were borderline positive or false negative in the BTA dipstick assay.

TABLE 8

COMPARISON OF 1A3 AND BTA LATEXES IN DIPSTICK ASSAYS

| | DIPSTICK REACTIVITY | | |
|---|---|---|---|
| SAMPLE ID | 1A3 Latex | BTA Latex | TCC STATUS |
| DS | + | + | TCC+ |
| SS | + | − | TCC+ |
| TB | + | + | TCC+ |
| GD | + | ± | TCC+ |
| CDU | + | − | TCC+ |
| LWN | + | ± | TCC± |
| ABB | − | − | TCC− |
| RG | − | − | TCC− |
| AN | − | − | TCC− |
| JK | − | − | TCC− |
| RT | − | − | TCC− |
| AM | − | − | TCC− |
| SG | − | − | Stage C1 Prostate CA |
| UTX025 | − | − | BPH/TCC− |
| IC | + | + | Stage D3 prostate CA |
| NR | + | + | Ureter Stone/TCC− |

1A3 antibody coated latex provided improved sensitivity over the normal BTA latex with comparable specificity on the small group of samples tested and provides an example of immunological detection of the complexes.

EXAMPLE 10

WESTERN BLOT REACTIVITY OF 1B4 AND OTHER CLONES WITH COMPLEXES ISOLATED FROM URINES OF BLADDER CANCER PATIENTS

Samples were run in SDS-PAGE gels according to Example 3 using ~10 μg/well of protein. Immobilon-P membranes were equilibrated in SDS-PAGE running buffer (25 mM TRIS, 192 mM glycine with 0.1% SDS) prior to the removal of the SDS-PAGE gel. Gels were then blotted onto the immobilon-P membrane using a BioRad Mini-Trans blot system. Electrophoretic transfer was performed at 250 mA constant for 2 hours. The membranes were then removed and placed in phosphate buffered saline containing 2% BSA as blocking agent for at least 2 hours at room temperature. The blot was then rinsed with phosphate buffered saline containing 0.1% Tween 20 (PBS-Tween). Antibody 1B4 or other clones (~2 μg/ml) was added in PBS-Tween and the membranes incubated for 2 hours at room temperature while gently rocking on a rotating rocker. The blot was then washed with PBS-Tween for 10 minutes. Alkaline phosphatase labeled goat anti-mouse antibody was now added in PBS-Tween for 60 minutes at room temperature. The blot was now washed three times for 10–15 minutes with PBS-Tween then washed two times in 50 mM TRIS, 5 mM $MgCl_2$, pH 9.0. Blots were developed using a BCIP/NBT substrate/Chromogen solution containing 100 μg BCIP/ml, 200 μg NBT/ml in 50 mM TRIS, 5 mM $MgCl_2$, pH 9.0. Band coloration was allowed to proceed until a pinkish background appears at which time the blots were washed in PBS-Tween and allowed to dry in the dark. Blots were scanned on a densitometer.

Figure 15A:
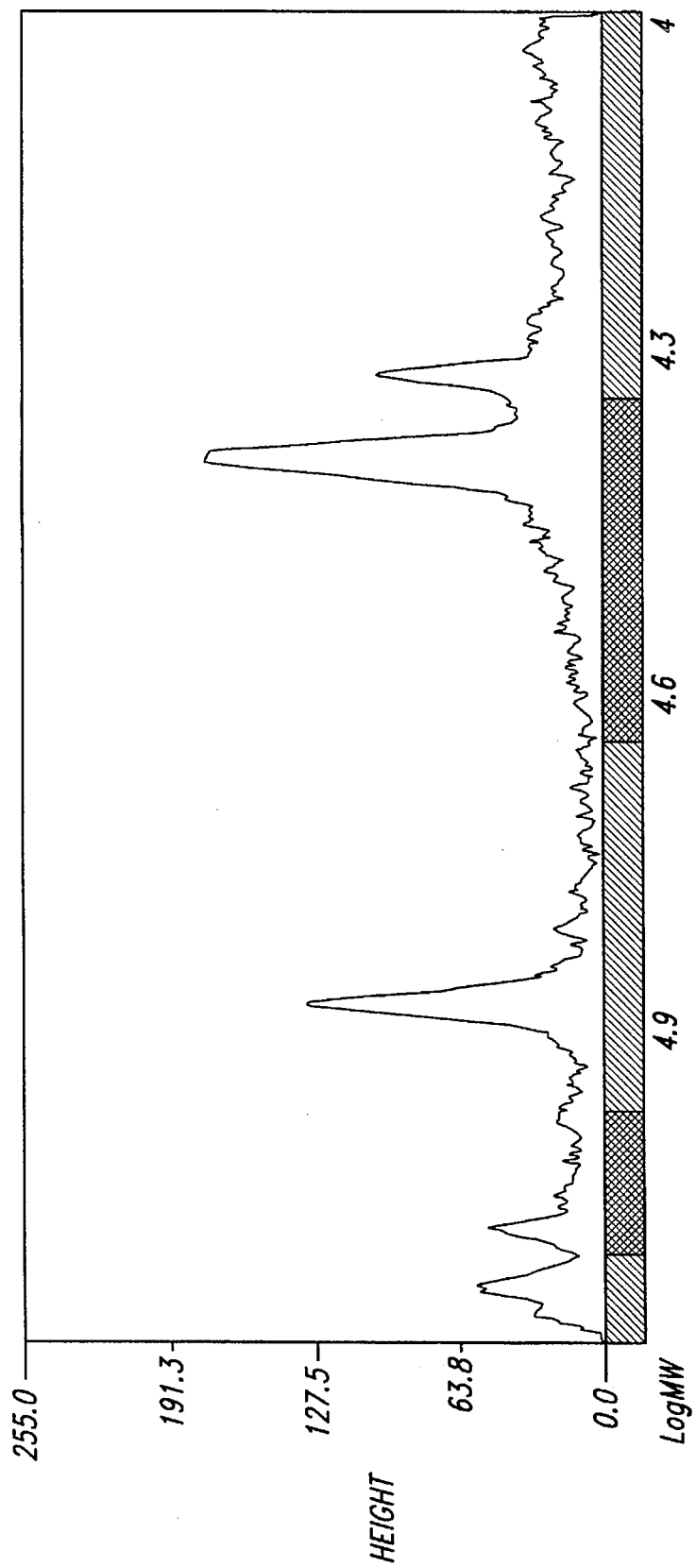
FIG. 15 graphically illustrates Western blot analyses of 1B4 antibody (Panel A) and related clones (such as 3D6, 12F3 and 8H2 which are Panel B) with complexes isolated from TCC positive urines as the solid phase antigen.
Figure 15B:
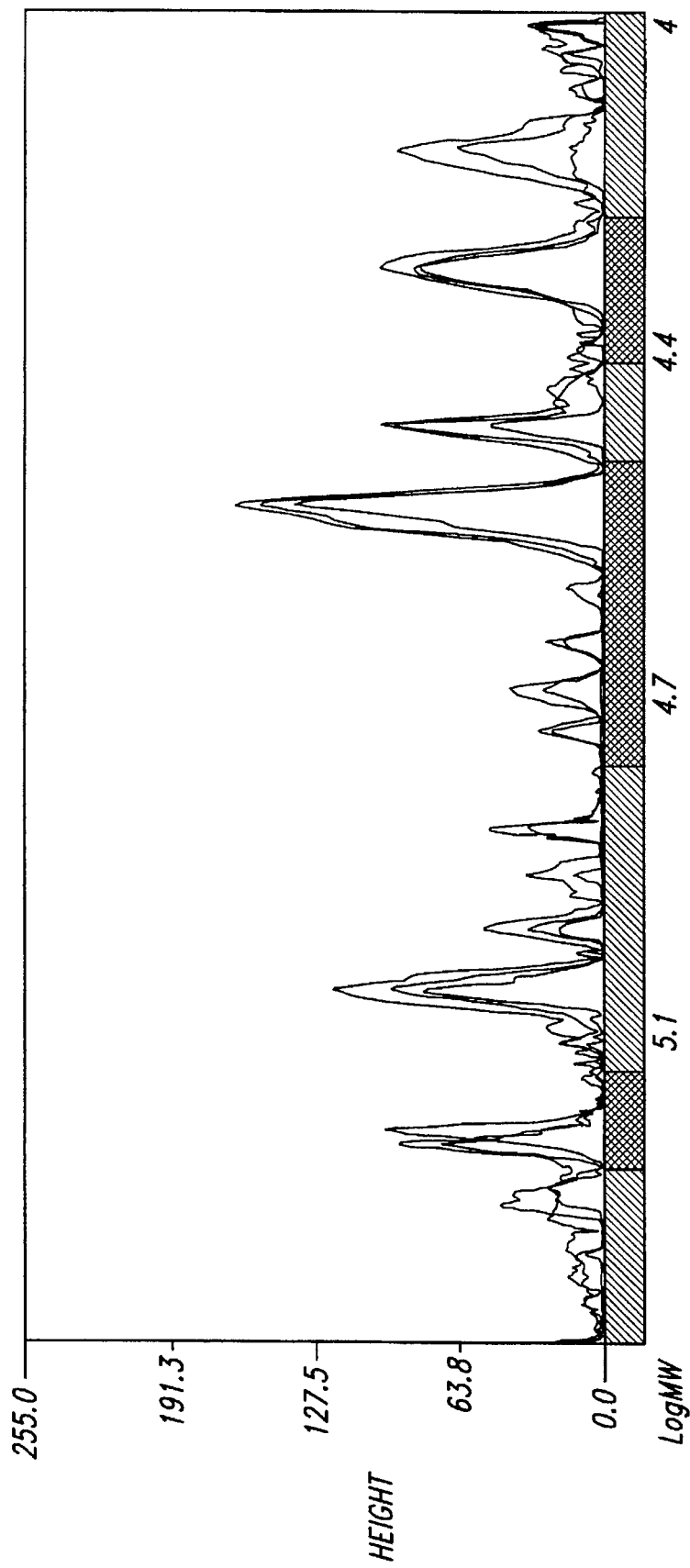

A Western blot for the 1B4 antibody on a 12% SDS-PAGE gel and related clones on an 11% SDS-PAGE gel versus TCC positive fractions is shown in FIG. 15, Panels A and B, respectively. A series of monoclonal antibodies to the BTA complexes isolated as described in Example 5 were used in Western Blot analyses as described above, using heparin agarose fractions from a patient with active TCC as the target antigen. Depending on antigen load, there are typically six bands that appear to be hit by the BTA monoclonal antibodies, depending on which clone is used. Monoclonal antibodies 1B4 and 3D6 hit bands at 82, 26, and 18 kd, with smaller bands at 98 kd, 32 kd and 165 kd upon higher antigen loads. Monoclonal antibodies 8H2 and 12F3 hit the same six main bands as 1B4, however, they hit the 98 kd and 32 kd stronger than 1B4. Occasionally there is evidence of a nonspecific band in the 16 kd region. All the BTA monoclonal antibodies tend to hit the higher molecular weight (165 kd) component of the complex upon higher antigen load. The data indicates that all four antibodies described hit the same complex but at different sites, and are reactive with epitopes that are present on interrelated components of a proteolytic degradation complex.

EXAMPLE 11

LATEX DIPSTICK AGGLUTINATION ASSAY FOR BASEMENT MEMBRANE COMPLEXES IN CERVICAL SECRETIONS

Cervical secretions were obtained from patients undergoing PAP smears and routine biopsy for dysplasia or cervical carcinoma in order to determine the relationship of the dipstick reactivity as described in Example 1 or the Heparin-ELISA reactivity with the 1B4 antibody similar to that described in Example 8.

Cervical secretions were obtained from patients prior to the PAP smear or any acetic washes. Samples were obtained using a cotton swab. Samples upon collection were then immersed in 100 µl of saline solution within a sealed tube for transportation to the laboratory. Samples were eluted off the swab as follows. Five hundred µgl of 20 mM Tris-buffered saline, pH 7.4, containing 25 mM EDTA and 2 mM Benzamidine was added to the sample and the swab vortexed for 2 minutes to elute the material. The mixture was then spun in a clinical benchtop centrifuge for 7 minutes at 7000 rpm to remove any cellular debris. Swabs are removed from the tube and discarded. The supernatants were now used to test for dipstick agglutination activity in this example and for testing in ELISA in the following example.

For testing dipstick activity doubling dilutions of the supernatant were prepared in the Tris buffered saline using 100 µl of the supernatant. Dilutions were then tested in the dipstick agglutination assay as described in Example 1. Thirty five µl of cervical supernatant or a dilution thereof were mixed with 35 µl of latex reagent. After mixing and incubating for 30 seconds, a dipstick was added and the reaction mix allowed to migrate up the dipstick. After 30 seconds the dipstick was read as positive or negative as described in Example 1. From this, the greatest dilution to which a sample remained positive was determined. This positive titer was then compared to the PAP smear and biopsy for each of samples to determine the relationship between dipstick activity and these other diagnostic procedures and to demonstrate that BTA activity was detectable in cervical secretions. Samples with a titer of ¼ or greater were considered positive. PAP smear data were determined as either Normal (PAP Class 1), Atypical (PAP Class 2), Dysplasia (PAP Class 3 or greater) or Carcinoma and confirmed with Biopsy.

TABLE 9

RELATIONSHIP OF PAP SMEAR/BIOPSY TO BTA DIPSTICK ACTIVITY IN CERVICAL SECRETIONS

| | BIOPSY/PAP SMEAR | | | |
|---|---|---|---|---|
| | Normals | Atypical | Dysplasis | Carcinoma |
| DIPSTICK | | | | |
| + | 3 | 2 | 7 | 4 |
| − | 32 | 4 | 4 | 0 |

The relationship between dipstick activity and PAP/Biopsy data is shown in Table 9 which demonstrates the ability of the dipstick to detect dysplasia as well as carcinoma. Positive titers for negative cervical secretions in the centrifuged supernatants were typically <½ but were as high as ¹⁄₆₄ in dysplasia and carcinoma patients. When related to the concentration in the undiluted secretions as collected on the original swab this constitutes titers of <¹⁄₁₄ and ¹⁄₄₅₀, respectively, because of the approximate ⅐ dilution due to elution volumes and assuming the swab volume of ~100 µl.

EXAMPLE 12

ELISA REACTIVITY OF 1B4 WITH CERVICAL SECRETIONS

Ninety-six well ELISA plates were coated overnight with 100 µl of heparin (4 µg/ml) in 50 mM carbonate/bicarbonate buffer, pH 9.6, and aspirated dry. Cervical secretions were prepared as described in Example 10. A ¹⁄₂₀ dilution of the cervical supernatant was prepared in 25 mM Tris-HCl buffer, pH 7.4. One hundred microliters of this dilution was added to a heparin-coated plates and incubated overnight at 4° C. or at 37° C. for 2 hours. Plates were then aspirated and 100 µl of phosphate buffered saline, pH 7.4, containing 2% bovine serum albumin was added to the wells and the plates incubated at room temperature for 90 minutes. Plates were then aspirated and 100 µl 1B4 antibody (1–2 µg/ml) was added to each of the wells and plates incubated for 2 hours at room temperature. Plates were then washed 3 times in phosphate buffered saline containing 0.1% Tween 20 prior to the addition of 100 µl of a ¹⁄₂₀₀₀ dilution of goat anti-mouse IgG-horse radish peroxidase (HRP) conjugate in phosphate buffered saline containing 0.1% Tween 20 and 0.1% bovine serum albumin. Plates were then incubated for 1 hour at room temperature then washed 3 times in PBS Tween. Detection of HRP labeled immunocomplexes in the wells was achieved by adding 100 µl of TMB substrate to the well incubating for 30 minutes at room temperature then stopping the reaction by adding 100 µl of 1N H$_2$SO$_4$. Wells were read at 450 nm in an ELISA reader.

TABLE 10

RELATIONSHIP OF PAP SMEAR/BIOPSY TO 1B4 ELSIA ACTIVITY IN CERVICAL SECRETIONS

| | PAP Smear/Biopsy | | | |
|---|---|---|---|---|
| | Normals | Atypical | Dysplasia | Carcinoma |
| 1B4 EIA | | | | |
| + | 1 | 3 | 9 | 4 |
| − | 34 | 3 | 2 | 0 |

Figure 16:
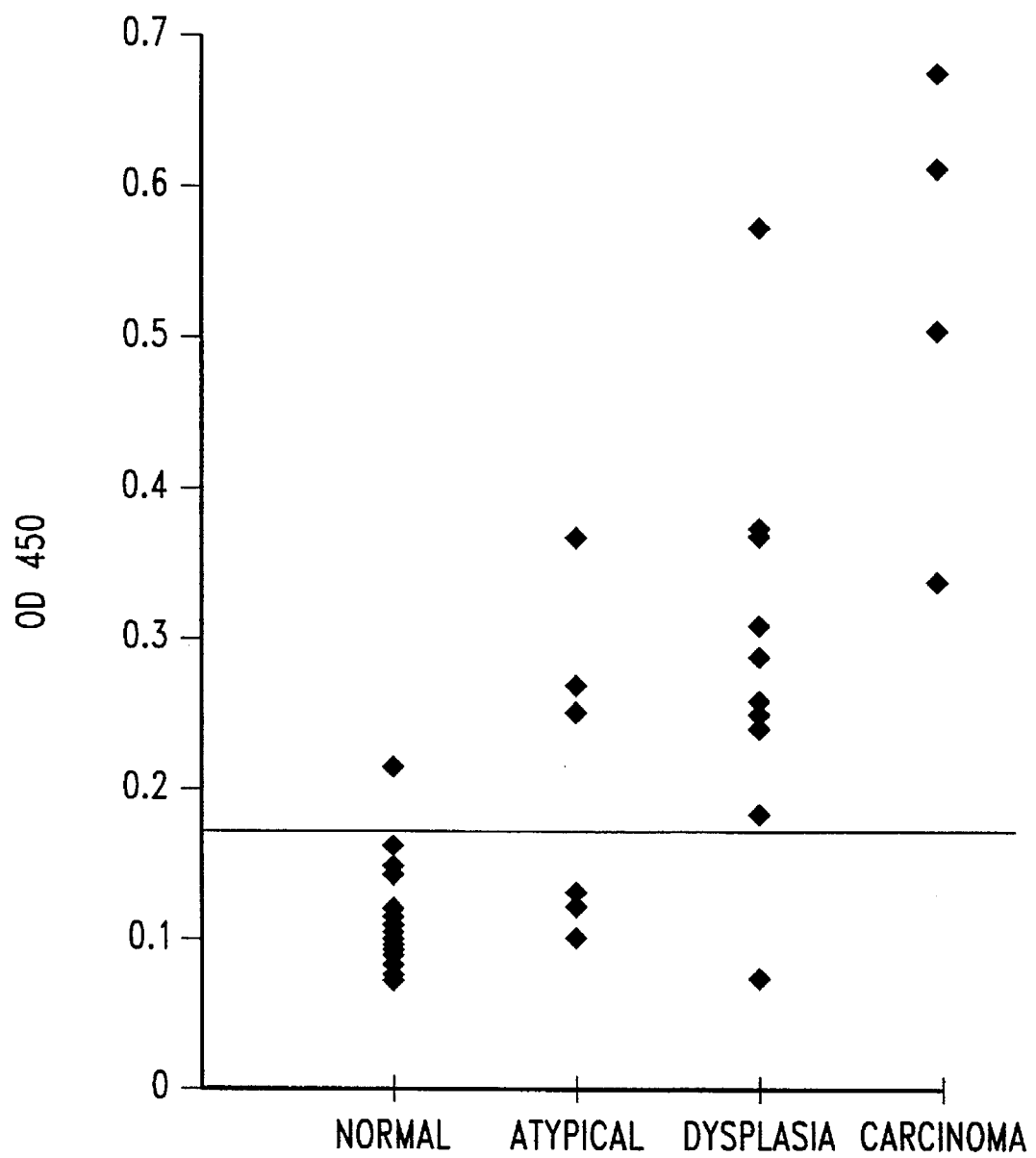
FIG. 16 graphically depicts reactivity of cervical secretions with 1B4 antibody in a heparin capture ELISA system and relationship to pap smear/biopsy data. A total of 35 patients were studied, with normal Class I pap smear, 6 with atypical Class II pap smear and 11 with Class III–V pap smear and 4 confirmed carcinoma patients.

The relationship between ELISA activity and PAP/Biopsy data is shown in Table 10 and the ELISA activity distributions are shown in FIG. 16 which demonstrates the ability of the assay to detect dysplasia as well as carcinoma.

From the foregoing, it will be appreciated that, although specific embodiments of the invention have been described herein for purposes of illustration, various modifications may be made without deviating from the spirit and scope of the invention.

We claim:

1. An antibody that specifically binds to a complex including basement membrane components, said complex being reactive with antibody 1B4 (ATCC No. 11389), and consisting of polypeptides with approximate molecular weights of 165,000; 140,000; 125,000; 98,000; 82,000; 74,000; 55,000; 43,000; 35,000; 26,000; and 16,000 as determined by sodium dodecyl sulfate-polyacrylamide gel electrophoresis.

2. The antibody of claim 1 wherein the antibody is a monoclonal antibody.

3. The cell line 1B4, designated by ATCC No. 11389.

4. A monoclonal antibody produced by the cell line of claim 3.

5. An antibody that specifically binds to a complex including basement membrane components, said complex being reactive with antibody 1B4 (ATCC No. 11389), and consisting of polypeptides with approximate molecular weights of 245,000; 190,000; 165,000; 140,000; 125,000; 98,000; 82,000; 74,000; 55,000; 43,000; 35,000; 26,000; and 16,000 as determined by sodium dodecyl sulfate-polyacrylamide gel electrophoresis.

6. The antibody of claim 5 wherein the antibody is a monoclonal antibody.

7. An antibody that specifically binds to a polypeptide having an approximate molecular weight of 165,000 as determined by sodium dodecyl sulfate-polyacrylamide gel electrophoresis, and to a complex including basement membrane components, said complex being reactive with antibody 1B4 (ATCC No. 11389), and consisting of polypeptides with approximate molecular weights of 165,000; 140,000; 125,000; 98,000; 82,000; 74,000.; 55,000; 43,000; 35,000; 26,000; and 16,000 as determined by sodium dodecyl sulfate-polyacrylamide gel electrophoresis.

8. An antibody that specifically binds to a polypeptide having an approximate molecular weight of 43,000 as determined by sodium dodecyl sulfate-polyacrylamide gel electrophoresis, and to a complex including basement membrane components, said complex being reactive with antibody 1B4 (ATCC No. 11389), and consisting of polypeptides with approximate molecular weights of 165,000; 140,000; 125,000; 98,000; 82,000; 74,000; 55,000; 43,000; 35,000; 26,000; and 16,000 as determined by sodium dodecyl sulfate-polyacrylamide gel electrophoresis.

9. An antibody that specifically binds to a polypeptide having an approximate molecular weight of 55,000 as determined by sodium dodecyl sulfate-polyacrylamide gel electrophoresis, and to a complex including basement membrane components, said complex being reactive with antibody 1B4 (ATCC No. 11389), and consisting of polypeptides with approximate molecular weights of 165,000; 140,000; 125,000; 98,000; 82,000; 74,000; 55,000; 43,000; 35,000; 26,000; and 16,000 as determined by sodium dodecyl sulfate-polyacrylamide gel electrophoresis.

10. An antibody that specifically binds to a polypeptide having an approximate molecular weight of 82,000 as determined by sodium dodecyl sulfate-polyacrylamide gel electrophoresis, and to a complex including basement membrane components, said complex being reactive with antibody 1B4 (ATCC No. 11389), and consisting of polypeptides with approximate molecular weigts of 165,000; 140,000; 125,000; 98,000; 82,000; 74,000; 55,000; 43,000; 35,000; 26,000; and 16,000 as determined by sodium dodecyl sulfate-polyacrylamide gggqel electrophoresis.

11. An antibody that specifically binds to a polypeptide having an approximate molecular weight of 98,000 as determined by sodium dodecyl sulfate-polyacrylamide gel electrophoresis, and to a complex including basement membrane components, said complex being reactive with antibody 1B4 (ATCC No. 11389), and consisting of polypeptides with approximate molecular weights of 165,000; 140,000; 125,000; 98,000; 82,000; 74,000; 55,000; 43,000; 35,000; 26,000; and 16,000 as determined by sodium dodecyl sulfate-polyacrylamide gel electrophoresis.

\* \* \* \* \*